(12) United States Patent
Pushkarev et al.

(10) Patent No.: US 11,834,397 B1
(45) Date of Patent: *Dec. 5, 2023

(54) MOLTEN SALT CATALYTIC COMPOSITIONS AND METHODS FOR THE CRACKING OF CARBON-CONTAINING FEEDSTOCKS

(71) Applicant: Braskem America, Inc., Philadelphia, PA (US)

(72) Inventors: Vladimir Pushkarev, Pittsburgh, PA (US); Uriah Kilgore, Pittsburgh, PA (US); Charles Ambrass, Pittsburgh, PA (US); Scott Mitchell, Pittsburgh, PA (US); Ishant Khurana, Pittsburgh, PA (US)

(73) Assignee: Braskem America, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/153,163

(22) Filed: Jan. 11, 2023

Related U.S. Application Data

(63) Continuation of application No. 17/334,474, filed on May 28, 2021, now Pat. No. 11,597,690.

(Continued)

(51) Int. Cl.
*C07C 4/02* (2006.01)
*C10G 1/08* (2006.01)
(Continued)

(52) U.S. Cl.
CPC .............. *C07C 4/025* (2013.01); *C10G 1/086* (2013.01); *C10G 11/02* (2013.01); *C10G 27/04* (2013.01);
(Continued)

(58) Field of Classification Search
CPC . C10G 1/08; C10G 1/086; C10G 1/10; C10G 9/34; C10G 11/02; C10G 27/00; C10G 27/04; C07C 4/025
See application file for complete search history.

(56) References Cited

U.S. PATENT DOCUMENTS 3,876,527 A 4/1975 Dugan et al.
3,979,332 A 9/1976 Kiovsky et al.
(Continued)

FOREIGN PATENT DOCUMENTS

GB 2 106 932 A 4/1983
WO WO-80/02151 A1 10/1980
(Continued)

OTHER PUBLICATIONS

Ai, N., et al., "Co-Production of Activated Carbon and Bio-Oil from Agricultural Residues by Molten Salt Pryolysis," BioResources, 8(2):1551-1562 (2013) (12 pages).
(Continued)

*Primary Examiner* — Renee Robinson
(74) *Attorney, Agent, or Firm* — Foley & Lardner LLP

(57) ABSTRACT

A catalyst composition includes a metal catalyst dispersed in a molten eutectic mixture of alkali metal or alkaline earth metal carbonates or hydroxides. A process for the catalytic cracking of hydrocarbons includes contacting in a reactor system a carbon-containing feedstock with at least one catalyst in the presence of oxygen to generate olefinic and/or aromatic compounds; and collecting the olefinic and/or aromatic compounds; wherein: the at least one catalyst includes a metal catalyst dispersed in a molten eutectic mixture of alkali metal or alkaline earth metal carbonates or hydroxides. A process for preparing the catalyst includes mixing metal catalyst precursors selected from transition metal compounds and rare-earth metal compounds and a eutectic mixture of alkali metal or alkaline earth metal
(Continued)

carbonates or hydroxides and heating it. A use of the catalyst in the catalytic cracking process of hydrocarbons.

23 Claims, 12 Drawing Sheets

Related U.S. Application Data

(60) Provisional application No. 63/032,210, filed on May 29, 2020.

(51) Int. Cl.
    *C10G 27/04*     (2006.01)
    *C10G 11/02*     (2006.01)

(52) U.S. Cl.
    CPC . *C10G 2300/1092* (2013.01); *C10G 2400/20* (2013.01); *C10G 2400/22* (2013.01)

(56) References Cited

U.S. PATENT DOCUMENTS

| | | | |
|---|---|---|---|
| 4,216,194 | A | 8/1980 | Regier |
| 4,898,845 | A | 2/1990 | Datta et al. |
| 11,046,892 | B1 | 6/2021 | Sofranko et al. |

FOREIGN PATENT DOCUMENTS

| | | |
|---|---|---|
| WO | WO-2004/072163 A1 | 8/2004 |
| WO | WO-2004/072208 A1 | 8/2004 |

OTHER PUBLICATIONS

Alamer, A.M., et al., "Molten Salt Pryolysis of Waste Polystyrene," B.S. Thesis, Worcester Polytechnic Institute (2014) (96 pages).

Bertolini, G.E., et al., "Value Recovery From Plastics Waste by Pyrolysis in Molten Salts," Conservation & Recycling, 10(4):331-343 (1987) (13 pages).

Chambers, C., et al., "Polymer Waste Reclamation by Pyrolysis in Molten Salts," Ind. Eng. Chem. Process Des. Dev., 23(4):648-654 (1984) (7 pages).

Chen, C., et al., "Coupled Experimental Study and Thermodynamic Modeling of Melting Point and Thermal Stability of $Li_2CO_3$—$Na_2CO_3$—$K_2CO_3$ Based Salts," J. of Solar Energy Eng., 136, 031017 (2014) (7 pages).

Fedorov, A., et al., "Studies of Recycling of Poly(vinyl chloride) in Molten Na, Ca || $NO_3$, OH Systems," ISRN Chem. Eng., 2012, 768134 (2012) (6 pages).

International Search Report and Written Opinion on PCT PCT/US2021/034982 dated Sep. 8, 2021.

Kamali, A.R., et al., "Molten salt conversion of polyethylene terephthalate waste into graphene nanostructures with high surface area and ultra-high electrical conductivity," Applied Surface Sci., 476:539-551 (2019) (13 pages).

Stelmachowski, M., "Conversion of waste rubber to the mixture of hydrocarbons in the reactor with molten metal," Energy Conversion and Manag., 50:1739-1745 (2009) (7 pages).

Stelmachowski, M., "Feedstock recycling of waste polymers by thermal cracking in molten metal: thermodynamic analysis," J. Mater Cycles Waste Manag., 16(2):211-218 (2014) (8 pages).

Stelmachowski, M., "Thermal conversion of waste polyolefins to the mixture of hydrocarbons in the reactor with molten metal bed," Energy Conversion and Manag., 51(10):2016-2024 (2010) (9 pages).

Stelmachowski, M., et al., "Thermal and Thermo-Catalytic Conversion of Waste Polyolefins to Fuel-Like Mixture of Hydrocarbons," Chem. and Process Eng., 33(1):185-198 (2012) (14 pages).

Su, J., et al., "Catalytic pryolysis of waste packaging polyethylene using $AlCl_3$—NaCl eutectic salt as catalyst," J. of Analytical and Applied Pyrolysis, 139:274-281 (2019) (8 pages).

Tekin, K., et al., "Catalytic degradation of waste polypropylene by pyrolysis," J. of the Energy Inst., 85(3):150-155 (2012) (6 pages).

US 11,834,397 B1

MOLTEN SALT CATALYTIC COMPOSITIONS AND METHODS FOR THE CRACKING OF CARBON-CONTAINING FEEDSTOCKS

CROSS-REFERENCE TO RELATED APPLICATIONS

This application is a continuation of U.S. patent application Ser. No. 17/334,474 filed on May 28, 2021, which claims the benefit of and priority to U.S. Provisional Application No. 63/032,210, filed May 29, 2020, the contents of which are incorporated herein by reference in their entirety.

FIELD

The present technology is generally related to catalysis for the cracking of carbon-containing feedstocks. More specifically, it is related to molten salt compositions for catalyst compositions and methods of cracking in the presence of an oxidant to form olefinic and aromatic monomers from a carbon-containing feedstock.

SUMMARY

Oxycracking is an attractive route for the direct conversion of carbon-containing feedstocks (e.g., waste plastics, bio-based complex compositions, light alkanes, and municipal solid waste) into value-added basic chemical building blocks (e.g., olefins, oxo-compounds, and aromatics). The direct conversion of carbon-containing feedstocks reduces carbon dioxide emissions usually associated with the production of value-added basic chemical building blocks. One way to perform oxycracking relies on the use of a molten salt catalyst, and the present inventors have found that the molten salt catalyst can improve the process efficiency.

In one aspect, a heterogeneous catalyst composition is provided that includes a metal catalyst dispersed in a molten salt matrix comprising a eutectic mixture of alkali metal or alkaline earth metal carbonates or hydroxides. In some embodiments, the metal catalyst includes a transition metal compound, a rare-earth metal compound, or a mixture of a transition metal compound and a rare-earth metal compound. In some embodiments, the eutectic mixture is a mixture of alkali metal or alkaline earth metal carbonates or hydroxides having a melting point of less than about 750° C.

In another aspect, a process is provided for catalytic cracking of hydrocarbons, where the process includes contacting in a reactor system a carbon-containing feedstock with at least one heterogeneous catalyst in the presence of an oxidant to generate olefinic and/or aromatic compounds; and collecting the olefinic and/or aromatic compounds; and wherein the at least one heterogeneous catalyst comprises a metal compound dispersed in a molten salt matrix of a eutectic mixture of alkali metal or alkaline earth metal carbonates or hydroxides. The process may be an autothermal process.

In another aspect, a process is provided for preparing a heterogeneous catalyst, where the process includes combining alkali metal or alkaline earth metal carbonates or hydroxides to form salt matrix comprising a eutectic salt mixture; adding to the salt matrix, at least one metal catalyst precursor to form a catalyst precursor mixture; and heating the catalyst precursor mixture to a temperature of about 250° C. to about 750° C. to form the heterogeneous catalyst comprising a metal catalyst dispersed in a molten salt matrix; wherein the metal catalyst precursor includes at least one transition metal compound, rare-earth metal compounds, or a combination of any two or more thereof.

DETAILED DESCRIPTION

Figure 1:
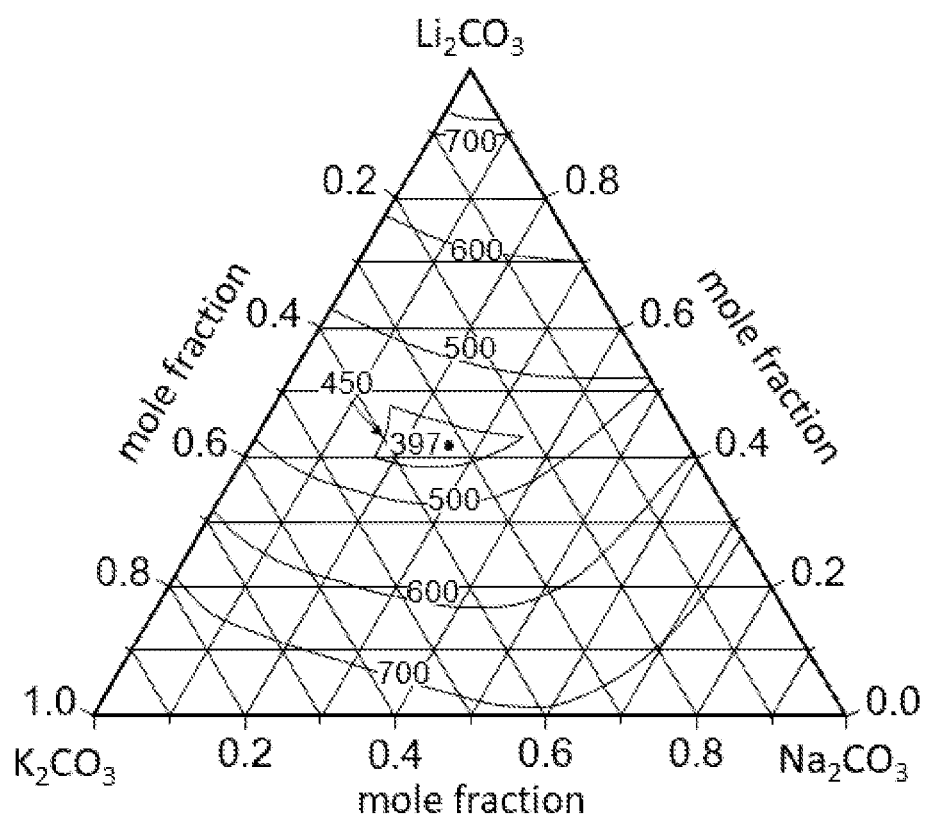
FIG. 1 is a ternary phase diagram for lithium, sodium, and potassium carbonates as reproduced from Chen et al. *J. Sol. Energy Eng.* 136(3): 031017 (August 2014).

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and may be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "dispersion" refers to a system in which particles of one material are distributed in a continuous phase of another material. The two phases may be in the same or different states of matter, i.e., a solid metal catalyst dispersed in a molten alkali metal or alkaline earth metal carbonate eutectic mixture melt. Dispersions are classified in several ways, including how large the dispersed particles are in relation to the particles of the continuous phase, and whether or not a spontaneous precipitation (sedimentation) occurs. In general, dispersions of particles sufficiently large for sedimentation are called suspensions, while those of smaller particles are called colloids, and even smaller are called solutions. In application to this invention the metal catalyst dispersed in the molten matrix can be a suspension, or it can be a colloid, or it can be a solution. The boundary between the cases of a bulk metal catalyst and a dispersed metal catalyst is in the average particle size of 10 mm (cross-section distance from one side to the other side for a particle). It can be said that a bulk metal catalyst has an average particle size of >10 mm, while a dispersed metal catalyst has an average particle size of ≤10 mm. Another commonly found descriptor for the boundary case is the geometric surface area of the dispersed material. In this case a bulk metal catalyst has a geometric surface area of <0.01 meter square per gram of metal catalyst material, while a dispersed metal catalyst has a geometric surface area of ≥0.01 meter square per gram of the metal catalyst material.

As used herein, the term "cracking" refers to a chemical process whereby a feedstock, i.e. complex organic molecules such as long-chain hydrocarbons, carbohydrates, or others are broken down into simpler molecules such as light hydrocarbons, oxygenates, or carbon oxides by the breaking of chemical bonds in the feedstock.

As used herein, the term "thermocracking" refers to a cracking process, whereby the conversion of feedstock to products is achieved by thermal energy transfer, i.e. heating, and, hence, it requires operating at elevated temperatures to proceed.

As used herein, the term "oxycracking" refers to a cracking process that utilizes a combination of thermocracking and oxidation processes, generally applied to the processing of heavy carbon-containing feedstocks, resulting in the formation of lighter hydrocarbons products, plus some amounts of organic oxygenates, CO, $CO_2$, and $H_2O$ as the co-products.

As used herein, the term "reactor system" refers to where the catalytic cracking reaction(s) take place. The process for catalytic cracking of hydrocarbons may occur in a single reactor or in at least two reactors in series.

As used herein, the term "at least one heterogeneous catalyst" refers to the possibility of introducing more than one heterogeneous catalyst in the reactor system of the process for catalytic cracking of hydrocarbons. Hence, one or more than one heterogeneous catalyst may be in contacted with the carbon-containing feedstock in a single reactor or separated in at least two reactors in series. At least one heterogeneous catalyst may be equal or different from each other.

As used herein, the term "carbon-containing feedstock" is not only purely hydrocarbon materials as would typically be associated with the term, but as long as there is a carbon-containing segment within a plastic (i.e. polymer) or biomass or biowaste that is amenable to cracking with the catalyst compositions provided herein, it meets the definition. For example, the carbon-containing feedstock may contain oxygen in the material, as well as other heteroatoms (N, P, S, Cl, etc.) and other materials such as fillers (including silica, zinc oxide, titanium oxide, calcium carbonate, etc.), colorants, plasticizers, and the like typically associated with polymers.

As used herein, the term "eutectic" or "eutectic mixture" refers to a homogeneous mixture of substances that melts or solidifies at a single temperature that is lower than the melting point of any of the constituents. It does not necessarily refer to the lowest melting point that is achievable with any particular mixture of substances, this is the eutectic point for those substances, and it may be part of the eutectic mixture. As long as a mixture of substances melts at a temperature lower than the melting point of any of its constituting pure substances, and forms a single continuous phase, it is a "eutectic" or "eutectic mixture" for the purposes of this disclosure. As used herein, the phrase "a eutectic mixture of alkali metal or alkaline earth metal carbonates or hydroxides" may be alternatively recited as "a eutectic mixture of alkali metal carbonates, alkali metal hydroxides, alkaline earth metal carbonates, alkaline earth hydroxides, or a mixture of any two or more thereof."

It has now been found that the cracking of carbon-containing feedstocks may be conducted in the presence of oxygen as an oxidant, which can be a free oxygen gas ($O_2$) or oxygen bound to catalyst, and a molten salt catalyst to form a product stream containing olefinic and/or aromatic compounds. The methods may be applied to carbon-containing feedstocks and includes recycling of olefinic polymers and biopolymers alike. The methods may be applied to pure hydrocarbon feedstock streams as well as mixed streams, particularly where the hydrocarbon stream is from a mixed waste recycling operation. The described methods and catalysts have the potential to deliver improved performance over industry accepted methods such as thermal pyrolysis, thermal-steam cracking, fluid catalytic cracking, and supercritical fluid cracking. The cracking of the hydrocarbons on the molten salt catalyst is a heterogeneous process, hence reference to a "heterogeneous catalyst" or "heterogeneous catalytic process." Where free oxygen gas ($O_2$) is used in the process, the process is called "direct oxycracking." Where the catalyst-bound oxygen is used in the process, the process is called "2-step oxycracking." In the 2-step oxy-cracking, the Step 1 is the reaction of a hydrocarbon feed with the catalyst-bound oxygen (i.e., metal oxide lattice oxygen, or surface adsorbed form of oxygen), which results in the loss of bound oxygen to the reaction products and the formation of an oxygen-deficient (e.g., spent) form of catalyst. The Step 2 is the reaction of catalyst regeneration where the oxygen-deficient form of the catalyst reacts with free oxygen gas to restore the catalyst to its native oxidized form. The catalyst in such a 2-step process also performs the function of an oxygen carrier.

The methods described herein take advantage of autothermal cracking processes where the thermal demands for the process are met by all, or at least part of, the internally generated heat by taking advantage of the exothermic process. Other accepted processes in the industry rely entirely on externally generated heat to achieve the desired conversion, and, because of this, are more energy and capital-intensive processes.

The present methods are also a fast-cracking process, due to the presence of both oxygen and molten catalyst, allowing for lower processing temperatures (i.e., less than 750° C.). Alternative cracking processes, such as thermal- and thermal-steam cracking, require a much higher temperature, typically greater than about 850° C., in order to achieve similar productivity output per reactor unit of volume. Further, the present methods require only a moderate pressure inside the reactor, i.e., less than about 20 atmospheres ("atm"). Alternative cracking processes, such as supercritical fluid cracking and high-pressure catalytic cracking, utilize much higher processing pressures, and, because of this, are more energy and capital-intensive processes.

The methods described herein also tolerate the presence of acid impurities, such as those containing chloride, bromide, sulfide, sulfate, and phosphate groups in the feed. The method also tolerates the presence of plastic filler components, such as silica, titania, zinc oxide, calcium carbonate, and others. The removal of such acid impurities and plastic filler components is believed to occur through the absorption of such materials into the eutectic mixture, which is then purified, and the impurities removed. Thus, the method is feedstock flexible and can be used to process mixed plastic waste. The methods may also be operated as a continuous, semi-continuous, or batch processes. Thus, the method offers a high degree of flexibility for its end-user application design and operation.

Without being bound by theory, the reaction is believed to proceed according to the following eight equations and summarized as equation (9). In equation (1) a catalytic oxycracking is described for a polyolefin feed reacting with oxygen in the presence of a catalyst at a temperature of less than about 750° C., or less than about 650° C. The catalyst is a molten salt mixture of alkali metal or alkaline earth metal carbonates or hydroxides with a metal catalyst. The product of the reaction is an aldehyde.

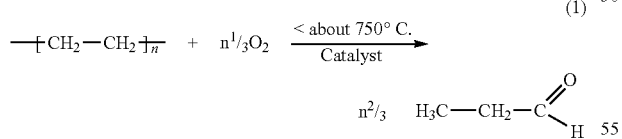

(1)

When a sufficient amount of oxygen is present, the aldehyde product from equation (1) can undergo further oxidation forming a carboxylic acid according to equation (2).

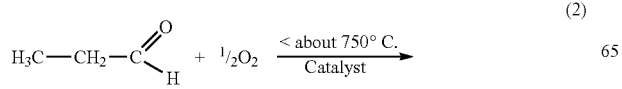

(2)

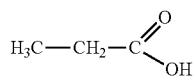

Within the same reactor, several other reactions as described by equations (3-4) are also believed to be taking place. Equation (3) is a deoxygenation reaction via the catalytic conversion of the aldehyde over the catalyst to the olefin, with carbon monoxide and hydrogen forming as co-products.

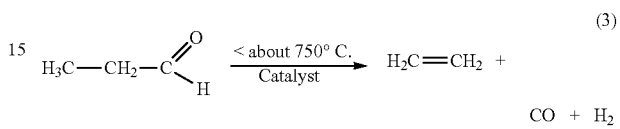

(3)

Equation (4) is a deoxygenation reaction via the catalytic conversion of the carboxylic acid over the catalyst to the olefin, with carbon dioxide and hydrogen as co-products.

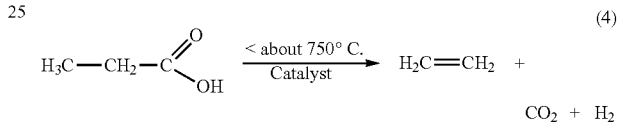

(4)

The catalyst, which is a molten salt mixture of alkali metal or alkaline earth metal carbonates or hydroxides with metal compound, can be a bifunctional catalyst, because it accelerates both oxycracking and deoxygenation reactions simultaneously.

Within the same reactor, several secondary reactions as described by equations (5-8) are also believed to be taking place. These reactions can proceed on their own or be accelerated by the presence of catalyst. Equation (5) is a hydrogenation reaction via the conversion of an olefin and hydrogen to an alkane.

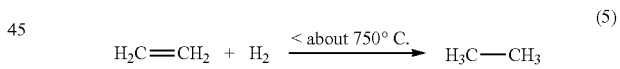

(5)

Equation (6) is a reverse water-gas shift reaction via the conversion of carbon dioxide and hydrogen to carbon monoxide and water.

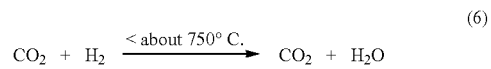

(6)

Equation (7) is a disproportionation, which is also known as the Boudouard reaction, reaction via the conversion of two equivalents of carbon monoxide to one equivalent of carbon dioxide and one equivalent of free carbon (i.e., coke).

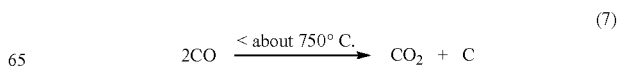

(7)

Finally, when certain excess of oxygen present, Equation (8) is an oxidation reaction via the conversion of one equivalent of free carbon with two equivalents of oxygen to one equivalent of carbon dioxide.

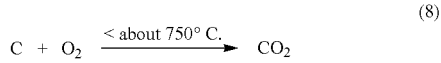

(8)

Catalyst can be selected such that the overall reaction is shown by reference to Equation (9):

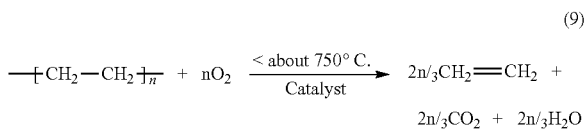

(9)

As provided in Equation (9), the overall reaction is exothermic and provides heat to sustain itself. The standard enthalpy of reaction for equation (9) is estimated to be approximately −97 kcal/mol. It is noteworthy that the thermal degradation of polyethylene (—($CH_2CH_2$)$_n$—) in the absence of the catalyst system and oxygen is an endothermic reaction having an enthalpy of reaction estimated as +25.4 kcal/mol.

In a first aspect, a heterogeneous catalyst composition is provided that includes a metal catalyst dispersed in a molten salt matrix of a eutectic mixture of alkali metal or alkaline earth metal carbonates or hydroxides. The metal catalyst may include at least one metal compound selected from the group of transition metal compounds, rare earth metal compounds, or a combination of any two or more thereof. The eutectic mixture is the basis for the molten salt matrix, and it melts at a lower temperature than its constituent materials, and it melts at a temperature at which the catalytic reactions may be conducted to form desirable materials from a feedstock.

The eutectic mixture of alkali metal carbonates and hydroxides may be a mixture of Li, Na, and K carbonates or hydroxides. In some embodiments, the eutectic mixture is one of $Li_2CO_3$, $Na_2CO_3$, and $K_2CO_3$. FIG. 1 is a phase diagram reproduced from Chunlin Chen, Ty Tran, Rene Olivares, Steven Wright, Shouyi Sun; J. Sol. Energy Eng. August 2014, 136(3): 031017, illustrating the melting points for a wide variety of Li, Na, and K carbonates mixtures. In some embodiments, the eutectic mixture of alkali metal carbonates or hydroxides has a melting point of less than about 750° C., or less than about 650° C. This includes melting points from about 250° C. to about 650° C., from about 350° C. to about 550° C., or about 400° C. Other illustrative eutectic mixture of alkali metal carbonates includes those in Table 1, reproduced from Mutch et al. *J. Mater. Chem. A* 7, 12951-12973 (2019).

TABLE 1

Melting points of the individual alkali-carbonate salt compounds and their eutectic mixtures.

| Salt System | Melting Point (° C.) |
|---|---|
| $Li_2CO_3$ | 723 |
| $Na_2CO_3$ | 854 |
| $K_2CO_3$ | 891 |
| $Li_2CO_3$—$Na_2CO_3$ (52-48 mol %) | 501 |
| $Li_2CO_3$—$K_2CO_3$ (62-38 mol %) | 498 |
| $Na_2CO_3$—$K_2CO_3$ (56-44 mol %) | 710 |
| $Li_2CO_3$—$Na_2CO_3$—$K_2CO_3$ (43.5-31.5-25 mol %) | 397 |
| $Na_2CO_3$—$BaCO_3$ (52.2-47.3 mol %) | 686 |

Where the eutectic mixture includes a hydroxide of Li, Na, and/or K at the beginning of a process employing such a mixture, it should be noted that the processes described herein generate $CO_2$ as a byproduct. Accordingly, with $CO_2$ generation at the operating temperatures of the molten salt, any alkali or alkaline earth metal hydroxides are readily converted to the corresponding carbonates.

In one embodiment, the transition metal compound that is included in the metal catalyst may include a transition metal having catalytic properties, and its incorporation into the catalyst composition may be as a transition metal carbonate, a transition metal salt of an organic acid, or a transition metal oxide. The transition metal may be based upon a Group 4-12 metal. Illustrative transition metals may include, but are not limited to, one or more of V, Cr, Mn, Fe, Co, Ni, Cu, Zn, Mo, and W. In some embodiments, the transition metal is one or more of Mn, Fe, Ni, Cu, Co, and W. In some embodiments, the transition metal compound may include a carbonate of one or more of Mn, Fe, Co, Ni, and Cu. In other embodiments, the transition metal compound may include a salt of an organic acid of one or more of Cr, Mn, Fe, Co, Ni, Cu, and Zn, where the organic acid is derived from formic acid, acetic acid, propionic acid, butyric acid, hexanoic acid, oxalic acid, tartaric acid, lactic acid, oleic acid. And, in further embodiments, the transition metal compound may include an oxide of one or more of V, Cr, Mn, Fe, Co, Ni, Cu, Zn, Mo, and W.

In one embodiment, the rare earth metal compound that is included in the catalyst may be introduced as a rare earth metal carbonate, a rare earth metal salt of an organic acid, or a rare earth metal oxide. Illustrative rare earth metals include, but are not limited to, one or more of La, Ce, Pr, and Nd. In some embodiments, the rare earth metal compound is a rare earth metal carbonate that is a carbonate of one or more of La, Ce, Pr, and Nd. In some embodiments, the rare earth metal carbonate is a carbonate of Ce. In other embodiments, the rare earth metal compound may include a salt of an organic acid of one or more of La, Ce, Pr, and Nd, where the organic acid is derived from formic acid, acetic acid, propionic acid, butyric acid, hexanoic acid, lactic acid, oleic acid. And, in further embodiments, the rare earth metal compound may include an oxide of one or more of La, Ce, Pr, and Nd. It is noted that under the conditions of the formation of the eutectic mixture and reactions described herein, the transition metal compounds or rare earth metal compounds, if other than a carbonate or oxide, is likely converted to the carbonate or oxide during the course of the reaction(s). Thus, the transition metal compounds, or rare earth metal compounds added to the mixture of salts may be a precursor to the carbonate or oxide catalyst.

In any of the embodiments herein, a mixture of a transition metal compound and a rare earth metal compound may include a mixture of Cu, and Ce, and the eutectic mixture of alkali metal carbonates or hydroxides includes a mixture of Li, Na, and K. As an illustrative example, in some embodiments, the transition metal compound includes a mixture of $CuCO_3$, and $Ce(CO_3)_2$. In some such embodiments, the eutectic mixture of alkali metal carbonates or hydroxides may include a mixture of $Li_2CO_3$, $Na_2CO_3$, and $K_2CO_3$. In other embodiments, the transition metal compound includes a mixture of $Cu_2(OH)_2CO_3$, and $Ce_2(CO_3)_3 \cdot xH_2O$, and the molten salt matrix $Li_2CO_3$, $Na_2CO_3$, and $K_2CO_3$. Where such compounds are present, the mixture of a transition metal compound and a rare-earth compound may include the Cu, and Ce in a mol % ratio of about 0.10-0.20:1.00, respectively. The molten salt may include the Li, Na, and K in a mol % ratio of about 43:32:25.

In any of the embodiments herein, a mixture of a transition metal compound may include a mixture of La and Fe, and the eutectic mixture of alkali metal carbonates or hydroxides includes a mixture of Li, Na, and K. As an illustrative example, in some embodiments, the transition metal compound includes a mixture of $La(OH)_3$, $Ba(CO_3)_2$, and $FeCO_3$. In some such embodiments, the eutectic mixture of alkali metal carbonates or hydroxides may include a mixture of $Li_2CO_3$, $Na_2CO_3$, and $K_2CO_3$. Where such compounds are present, the mixture of a transition metal compound and rare earth metal compound may include the La, Ba and Fe in a mol % ratio of about 0.03-0.04:0.03-0.04:1.00, respectively. The molten salt may include the Li, Na, and K in a mol % ratio of about 43:32:25.

Before describing the process in more detail, as well as the reactor, it is noted that, overall, the process described herein is an oxycracking process. In other words, it is an oxygen-assisted thermocracking of hydrocarbons. Like conventional thermocracking, the method is capable of producing light olefins and aromatic hydrocarbons as its primary output, but at relatively lower process temperatures, which can result in an economic benefit to the practitioner. The use of oxidant as a process co-feed is needed in making the cracking reaction inside the volume net-exothermic, i.e., self-heating. This enables the reaction to produce comparable product yields at lower temperatures due to higher thermal efficiency. Albeit, this benefit comes as a cost, as a fraction of the hydrocarbon feed is now consumed as a form of internal fuel to generate the necessary heat. While for processing some type of feeds, this feed loss is economically detrimental, for processing of waste plastics, bio-wastes, and other low-quality feeds, the economic benefit can be significant. This economic benefit can further be improved by applying a catalyst to the oxycracking process that has been specifically designed to maximize the yield of light olefin and aromatics products; minimize the yield of the reaction byproducts such as alkanes, organic oxygenates and heavies; and to solve technical hurdles that are specific to the processing of waste plastics streams, including the presence of heteroatom functionalities, fillers, modifiers, etc. in the process feed.

In the oxycracking process, a carbon-containing feedstock is injected into a reactor system where it comes into contact with a form of oxygen, which can be either a free oxygen gas ($O_2$), or a catalyst-bound form of oxygen, or both, and a catalyst. The upper temperature limit within the reactor is defined by the need to preserve a substantial fraction of the carbon-carbon bonds of the feed from the thermo-pyrolytic decomposition. For example, for a polyethylene feed, the limit is defined by a ceiling temperature of about 610° C. For those familiar with the art, a commercial process designed for thermocracking of polyethylene can operate at a temperature exceeding the ceiling temperature by 50-150° C. in order to achieve economically practical feed-to-monomers conversion rates. In the case of other feeds, the upper temperature limit is a function of the ceiling temperatures of the corresponding monomers, as given in the values in Table 2, reproduced from Stevens, M.P. Polymer Chemistry an Introduction (3rd ed.). New York: Oxford University Press. pp. 193-194 (1999), plus the additional 50-150° C. to achieve practical rates:

TABLE 2

Ceiling temperatures of common hydrocarbon monomers.

| Monomer | Ceiling Temperature (° C.) | Structure |
|---|---|---|
| ethylene | 610 | $CH_2=CH_2$ |
| 1,3-butadiene | 585 | $CH_2=CHCH=CH_2$ |
| isoprene | 466 | $CH_2=C(Me)CH=CH_2$ |
| styrene | 395 | $PhCH=CH_2$ |
| methyl methacrylate | 198 | $CH_2=C(Me)CO_2Me$ |
| isobutylene | 175 | $CH_2=CMe_2$ |
| α-methylstyrene | 66 | $PhC(Me)=CH_2$ |

The lower temperature limit is defined by the need to maintain the catalyst in the liquid state. As an illustration, this is about 397° C. for the $Li_2CO_3$—$Na_2CO_3$—$K_2CO_3$ (43.5-31.5-25 mol %) eutectic mixture, about 283° C. for a NaOH—$Na_2CO_3$ (90-10 mol %) eutectic, about 360° C. for a KOH—$K_2CO_3$ (90-10 mol %) eutectic, about 170° C. for a NaOH—KOH (57-43 mol %) eutectic, and about 226° C. for a LiOH—KOH (30-70 mol %) eutectic. Because the underlying chemistry, in essence, is a partial oxidation, the reaction rate benefits from an increased pressure of oxygen gas in the feed. In practical terms, the oxycracking process can be performed from a sub-atmospheric to a moderately elevated pressure (20 atm) range of the oxygen gas (i.e., air) feed in order to minimize the risk of thermal run-aways for the safety reasons.

In another aspect, a process for the catalytic cracking of hydrocarbons is provided that incorporates any of the described catalyst compositions. The process may include contacting in a reactor a carbon-containing feedstock with at least one catalyst composition, in the presence of oxygen, to generate olefinic and/or aromatic compounds. The process further includes collecting the olefinic and/or aromatic compounds. As noted above, at least one catalyst is any of those as described herein and it may include a metal catalyst dispersed in a molten salt matrix comprising a eutectic mixture of alkali metal or alkaline earth metal carbonates. In some embodiments, this may include a mixture of a transition metal compound and a rare earth metal compound and a eutectic mixture of alkali metal carbonates or hydroxides. The $O_2$ gas may be introduced to the reactor/reaction as a purified $O_2$ stream, air, or a mixture of $O_2$ or air with a diluent gas, wherein the diluent is methane, carbon dioxide, nitrogen, argon, helium, or a combination of any two or more thereof.

The process provides for the production of olefinic and/or aromatic compounds from a carbon-containing feedstock. Because the carbon-containing feedstock may be from a wide variety of materials for process, including the processing of recycled plastics, biomass, biowaste, mixed plastics, biomass, and/or biowaste, the olefinic and/or aromatic compounds that are produced may include a wide variety of unsaturated compounds such as, but not limited to light olefins, α-olefins, terminal dienes, substituted and unsubstituted aromatic compounds, including single aromatic ring or several aromatic ring compounds.

Illustrative olefinic and/or aromatic compounds are from a wide range of materials. In some embodiments, the olefinic compounds may be from $C_2$ to $C_{20}$ olefins, from $C_2$ to $C_{16}$ olefins, or from $C_2$ to $C_{12}$ olefins, or from subranges of any of these. In some embodiments, the aromatic compounds may be from $C_6$ to $C_{18}$ aromatics, or from $C_6$ to $C_{12}$ aromatics, or from subranges of any of these. Illustrative olefinic and/or aromatic compounds include, but are not limited to, ethene, propene, 1-butene, 2-methyl-but-1-ene, 1-n-pentene, 2-methyl-pent-1-ene, 3-methyl-pent-1-ene, 1,3-butadiene, 1,3-pentadiene, 1,4-pentadiene, 1,3-hexadiene, 1,4-hexadiene, 1,5-hexadiene, benzene, toluene, ethylbenzene, xylenes, styrene, α-methylstyrene, naphthalene, and anthracene.

As noted herein, the carbon-containing feedstock may include, but is not limited to, any one or more of a refinery range hydrocarbons, a polymer, a biopolymer, biomass, or biowaste. Where the feedstock includes a polymer, illustrative polymers include, but are not limited to those such as polyethylene, polypropylene, polyisobutylene, polybutadiene, polystyrene, poly-α-methylstyrene, polacrylates, poly(meth)acrylates, polyvinyl acetate, and polyvinylchloride. Where the feedstock includes a biopolymer or other bio-based material it may include materials such as fatty acids, triglyceride esters of fatty acids, cellulose, lignin, sugars, animal fat, tissue, and ordure.

Refinery range hydrocarbons are typically defined by their boiling point range fractions. For example, light naphtha has an approximate boiling point range of 25 to 85° C., heavy naphtha has an approximate boiling point range of 85 to 200° C., kerosene has an approximate boiling point range of 170 to 265° C., gas oil has an approximate boiling point range of 175 to 345° C., and heavy residue has an approximate boiling point range of 345 to 656° C. All of these may serve as the feedstock for a refinery range hydrocarbon. In some embodiments where the feedstock includes a refinery range hydrocarbon, it may include asphalt, vacuum resid, heavy residual oil, paraffin wax, lubricating oil, diesel, kerosene, naphtha, or gasoline. In some embodiments, the feedstock may include n-hexane, n-hexadecane, or white mineral oil.

Figure 2:
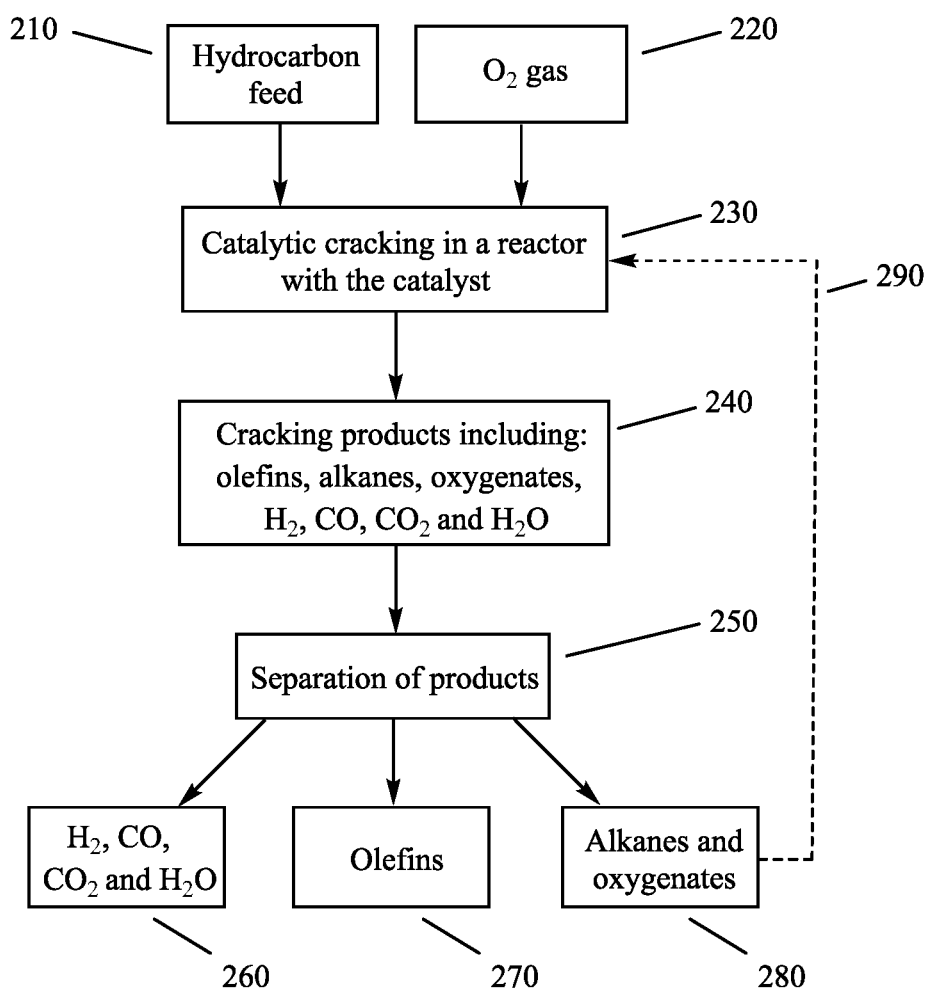
FIG. 2 is a flow chart for one embodiment of the method of cracking using a heterogeneous catalyst composition described herein.

The process described herein may be generally described by reference to FIGS. 2 and 3. As shown, the process 200, 300 includes introducing a carbon-containing feedstock 210 to a reactor. Oxygen gas (as $O_2$, air, or other gas mixtures containing $O_2$) 220 may be co-fed to the reactor 230 that contains a catalyst comprised of a metal compound dispersed in a molten salt matrix of a eutectic mixture of alkali metal or alkaline earth metal carbonates or hydroxides, and the carbon-containing feedstock undergoes catalytic cracking with oxygen to generate products of the reaction 240. The products of the reaction include light olefins, other hydrocarbons such as alkanes and oxygenates, hydrogen, carbon monoxide, carbon dioxide, water, and the like. The products are then separated 250 by any of distillation, membrane separation, pressure swing adsorption, or a combination of any two or more thereof, as appropriate. As part of the separation, each of the products may be separated into a product stream, three of which are shown in FIG. 2 as $H_2$, CO, $CO_2$ plus $H_2O$ 260, olefins 270, and alkanes and oxygenated organic compounds 280. The olefins, of course, may be collected for use in preparing virgin polymers, or in other applications. The alkane byproducts, together with the oxygenates, which are composed mostly of low carbon atom aldehydes such as acetaldehyde and others, as well as ketones such as acetone may be used industrially in appropriate applications; or hydrogenated to alcohols; or recycled back into the cracking process using the optional recycling loop 290 for the additional conversion to the desired olefins.

Figure 3:
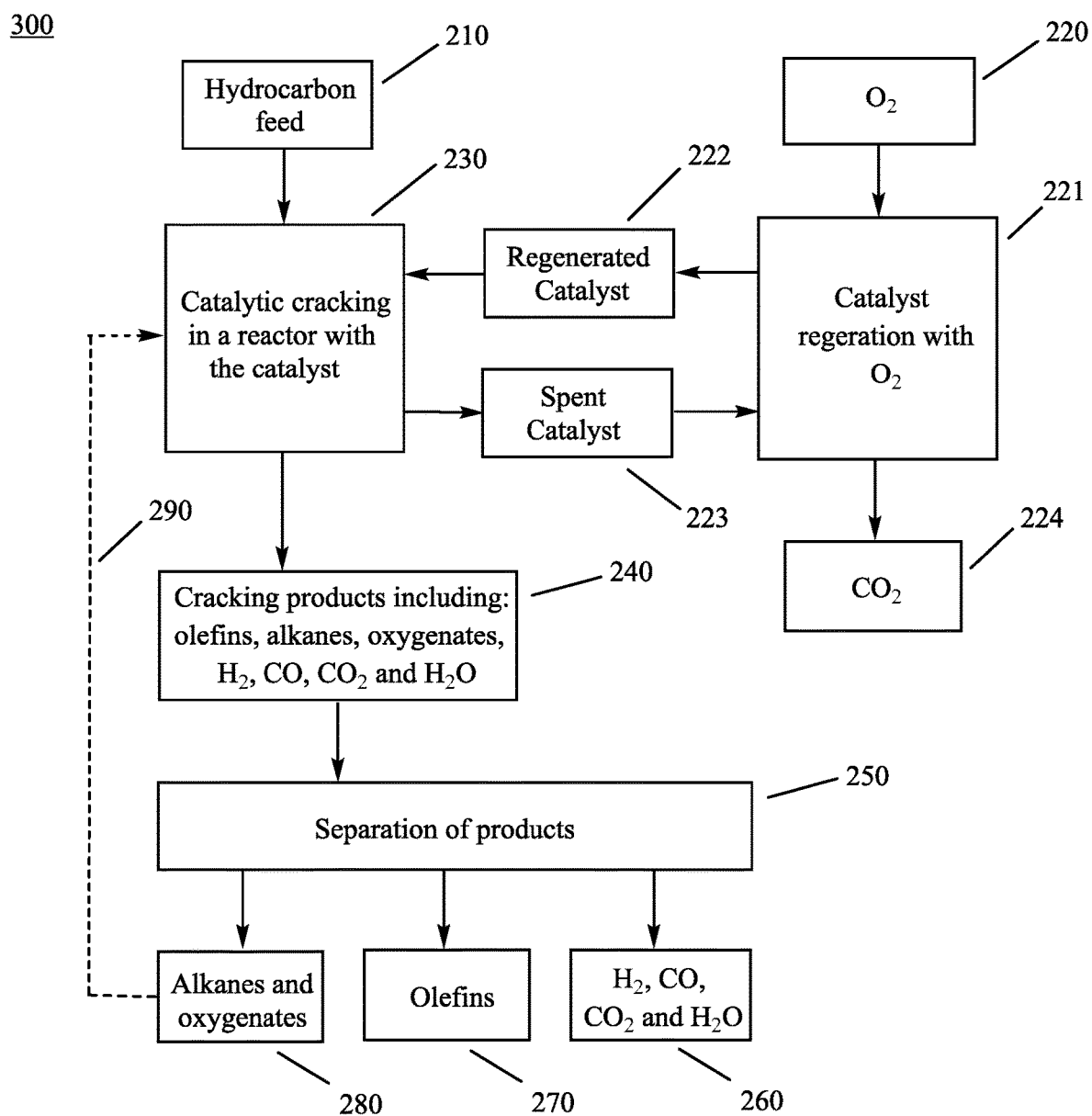
FIG. 3 is a flow chart for another embodiment of the method of cracking using a heterogeneous catalyst composition as described herein and including a catalyst regeneration loop.

As illustrated in FIG. 3, the process may also include a catalyst recycling loop where spent molten salt catalyst 223 is moved to a catalyst regeneration reactor 221 where oxygen (as $O_2$, air, or other gas mixtures containing $O_2$) is reacted with the spent molten salt catalyst. Gases 224 that do not react with the spent molten salt catalyst such as nitrogen gas from air or are a result of the regeneration of the catalyst, may be vented, and the regenerated molten salt catalyst is then returned 222 to the reactor 230.

In the process, the temperature inside the reactor system is dependent upon the composition of the catalyst, feed, and desired reaction products. Accordingly, the temperature may be from the melting point of the eutectic mixture of alkali carbonates and/or hydroxides up to about 750° C. This may include a temperature from about 250° C. to about 750° C.

In the process, the pressures inside the reactor system may be low by comparison to other similar processes. For example, it may be about 20 atm or less. In some embodiments, it is from less than 1 atm to about 20 atm, from about 1 atm to about 15, or from about 2 atm to about 10 atm.

In the process, the at least one heterogeneous catalyst may be prepared outside of the reactor system; then loaded into the reactor system to carry out the catalytic cracking of hydrocarbons.

In another embodiment of the process, the at least one heterogeneous catalyst is prepared inside the reactor system, by loading the reactor system volume with a catalyst precursor mixture and heating it internally at the process temperature. The catalyst precursor mixture comprises a salt matrix comprising a eutectic mixture of a mixture of alkali metal or alkaline earth metal carbonates or hydroxides and a metal catalyst precursor comprising at least one metal compound selected from transition metal compounds, rare-earth metal compounds, or a combination of any two or more thereof.

Also provided is a process for preparing a heterogeneous catalyst. The process includes combining alkali metal or alkaline earth metal carbonates or hydroxides to form a salt matrix comprising eutectic salt mixture; adding to the salt matrix, at least one metal catalyst precursor to form a catalyst precursor mixture; and heating the catalyst precursor mixture to a temperature of about 250° C. to about 750° C. to form the heterogeneous catalyst comprising a metal catalyst dispersed in a molten salt matrix. In the process, the metal catalyst precursor comprises at least one metal compound selected from transition metal compounds, rare-earth metal compounds, or a combination of any two or more thereof, and the molten salt may also be in a precursor form as noted above, i.e., the hydroxide form. As noted above, the metal catalyst may include carbonates or oxide, and it may also include other oxide structures for the metals such as perovskites and spinels.

The heterogeneous catalyst produced by the process described above is useful in the process of catalytic cracking of hydrocarbons. Such a process of forming the catalyst may be conducted separately (ex-situ) from the process of cracking a hydrocarbon feedstock, or it may be done in the reactor system (in-situ) in which the cracking is conducted. While the in-situ process may be convenient for a batch type reaction, ex-situ processes are more convenient for continuous processes.

The reactor system for the proof of concept was a batch reactor and a stirred tank reactor. However, other suitable reactor configurations are considered such as falling film column reactors, packed column reactor, plate column reactor, spray tower reactor, and a variety of gas-liquid agitated vessel reactors.

Figure 4:
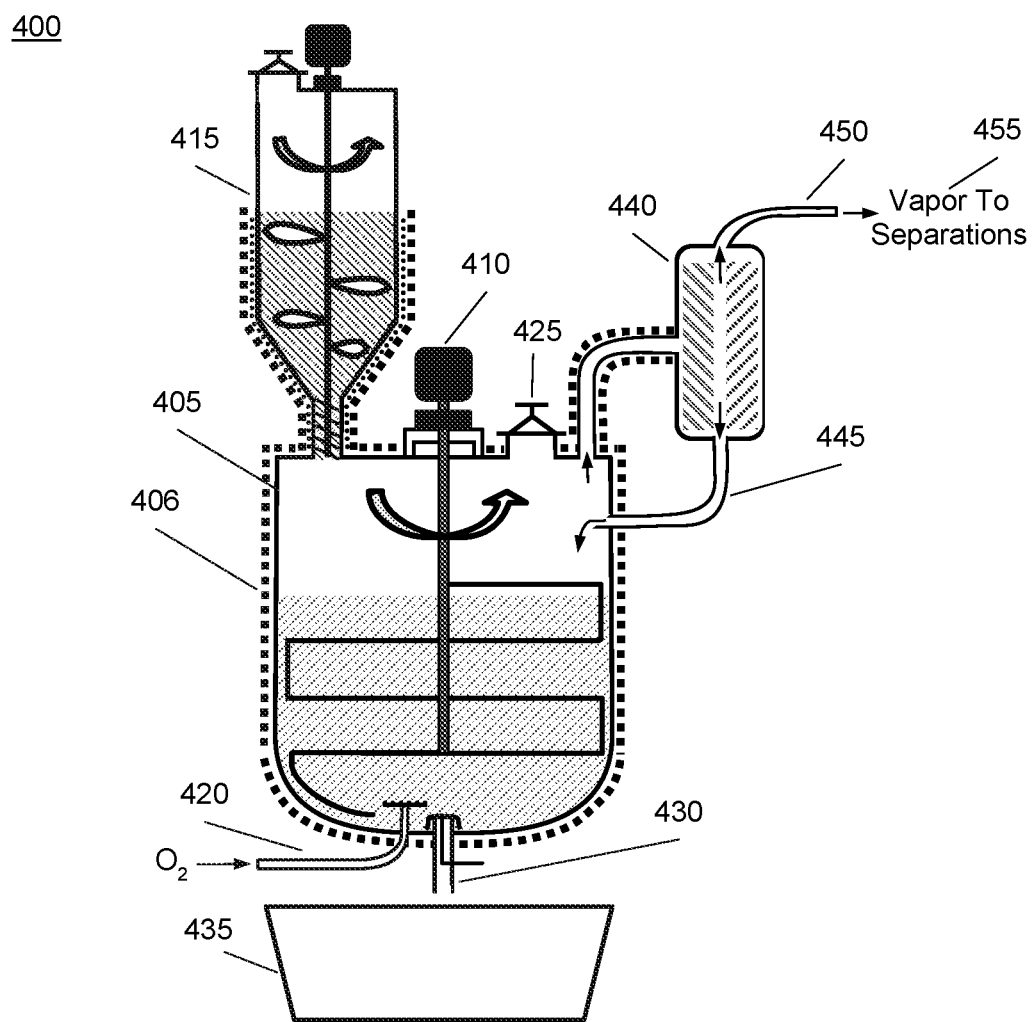
FIG. 4 is a general schematic representation of a reactor system for the processing of polymer waste.

Referring now to FIG. 4, a general schematic representation of a reactor system 400 for processing of polymer waste. The reactor tank 405, which is enclosed in the thermal insulation 406, is equipped with a motor and agitation system 410, an $O_2$ gas enters the reactor through the inlet and supply manifold 420, a catalyst loading port 425 and a catalyst offloading port 430. The catalyst composition is loaded into the reactor tank 405 via port 425. Polymer waste is chopped and loaded into a feeder which contains a heated Auger screw extruder 415 through which the polymer is introduced to the reactor tank 405. The reactor is maintained at a temperature sufficient to maintain the catalyst system as a molten salt. Solid wastes that are not catalytically converted, and solid impurities from the polymer may exit the reactor together with the aged catalyst via the port 430 into a holding drum 435. Gaseous products stream exits the reactor 405 and enters a separator 440. Condensed liquid stream of heavy products 445 (ex. compounds with the dew point above 120° C.) is returned from the separator into the reactor, while the gaseous stream 450 is directed towards the further separations.

The present invention, thus generally described, will be understood more readily by reference to the following examples, which are provided by way of illustration and are not intended to be limiting of the present invention.

EXAMPLES

Figure 6:
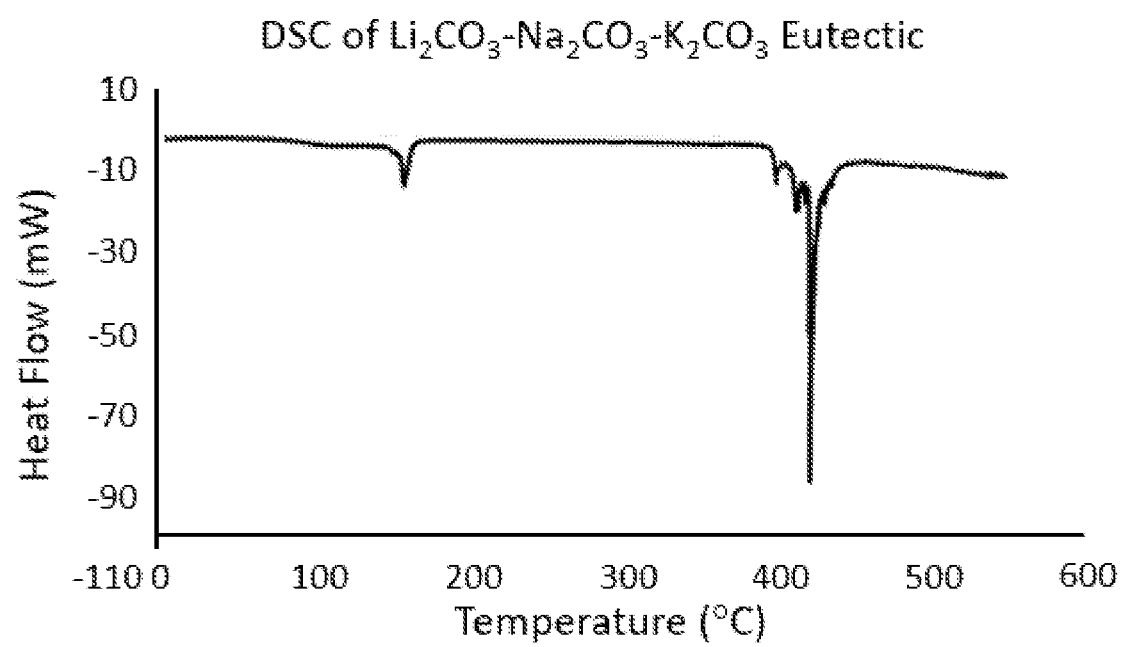
FIG. 6 is a differential scanning calorimetry (DSC) trace for the formation of a eutectic melt from a mixture of $Li_2CO_3$, $Na_2CO_3$, and $K_2CO_3$ powders, according to the examples.
Figure 7:
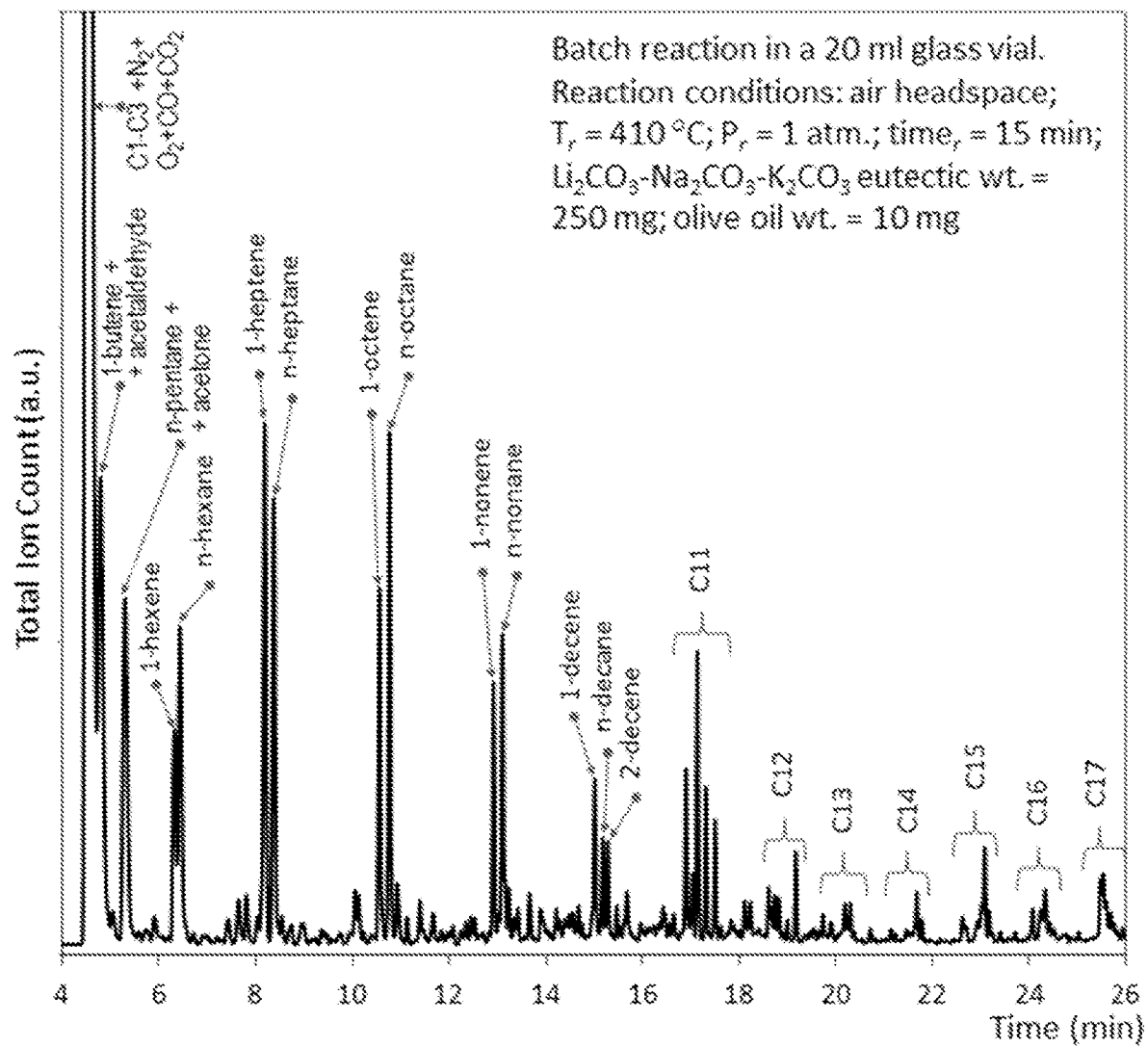
FIG. 7 is a representative GC-MS (gas chromatography-mass spectrometry) trace showing the peak assignments based on the mass-spectra signatures match with the NIST-MS database for an experiment of direct oxycracking of a vegetable (olive) oil over the $Li_2CO_3$—$Na_2CO_3$—$K_2CO_3$ (43.5-31.5-25 mol %) eutectic mixture in a mini-batch reactor. The experimental conditions are described in the upper right corner insert box.

Example 1. The Catalysts Used in the Study were Prepared by the Following Procedure Catalyst synthesis for the mini-batch reactor screening study: $Li_2CO_3$ (25.68 g), $Na_2CO_3$ (26.72 g), and $K_2CO_3$ (27.60 g) were added to a two-liter mixing vessel for thorough mixing. This mixture is compositionally similar to a eutectic mixture of the materials in the phase diagram (FIG. 1) that melts at about 397° C., and may be described by the chemical formula: $Li_{0.86}Na_{0.64}K_{0.50}CO_3$. The melting temperature was confirmed by a differential scanning calorimetry (DSC) analysis. FIG. 6 illustrates the DSC trace for the heating of 25 mg sample of the Li, Na, and K carbonates mixture at 20° C. per minute heating rate. At about 160-165° C., the water of hydration is released, and the three peak grouping (397° C., 408° C., and 420° C.) represents the three stages of melting of the precursor salts, a process that is kinetically limited when starting with a mixture of individual precursor salt powders, resulting in the formation of a single-phase eutectic melt at above 420° C. A molten salt catalyst is prepared by combining 80.00 g of this carbonate eutectic mixture with the $Li_{0.86}Na_{0.64}K_{0.50}CO_3$ eutectic composition; plus 0.40-18.00 g of each of the active metal precursor compound that is intended for the formulation inside the mini-batch reactor; before mixing with the eutectic composition, this mixture of catalyst metal precursor compounds is calcined in air at 600° C. for 2 hrs (for the off-gas evolution, believed to be primarily steam from the crystal hydride dehydration and $CO_2$ from the transition or rare-earth metal carbonate precursors conversion to a metal oxide form in the final catalyst state). For instance, one molten salt catalyst formulation contained about 80.00 g of the eutectic mixture of alkali carbonate salts and 1.00 g of a barium (II) carbonate powder ($BaCO_3$), plus about 1.00 g of a copper (II) carbonate powder ($CuCO_3 \cdot Cu(OH)_2$) and 17.00 g of cerium (III) carbonate powder ($Ce_2(CO_3)_3$). Another molten salt catalyst formulation contained about 80.00 g of the eutectic mixture of alkali carbonate salts and 0.40 g of $BaCO_3$, plus about 0.40 g of $La_2(CO_3)_3$, and 6.80 g of $FeCO_3$. Yet, another catalyst formulation contained about 80.00 g of the eutectic mixture of alkali carbonate salts and 0.40 g of $BaCO_3$, plus about 7.20 g of $MnCO_3$. Table 3 contains the description of catalyst formulations prepared for the screening study.

Catalyst synthesis for the continuously stirred tank reactor study: First, $Li_2CO_3$ (642.0 g), $Na_2CO_3$ (668.0 g), and $K_2CO_3$ (690.0 g) were added to a two-liter volume mixing vessel, where it was mixed thoroughly to make the alkali-carbonate salts mixture. Then, 25.0 g of $Cu_2(OH)_2CO_3$, 25.0 g of alkali-carbonate eutectic salts mixture, and 425.0 g of $Ce_2(CO_3)_3 \cdot xH_2O$ precursor powders were weighted into one liter volume mixing vessel, where it was mixed thoroughly to make the metal catalyst precursors mixture. The content of the vessel was poured into two 500 ml volume porcelain crucibles. The crucibles were placed into a calcination oven and calcined at 600° C. for 2 hours ("hr") using a heating-cooling ramp of 5° C./min. The calcination resulted in 18.7 wt % weight loss of the original metal catalyst precursors mixture due to decomposition of the carbonates to oxides and the loss of crystal hydride water. Lastly, the resulting 386.0 g of the metal catalyst powder was mixed in with 1930.0 g of the alkali-carbonate salts eutectic powders mixture inside the continuously stirred tank reactor vessel immediately before the reaction study.

TABLE 3

Description of catalyst formulations used in the oxycracking screening study.

| Catalyst | Precursor Compound Name | Weight, g |
|---|---|---|
| Eu = $Li_{0.86}Na_{0.64}K_{0.50}CO_3$ | $Li_2CO_3$ | 25.68 |
|  | $Na_2CO_3$ | 26.72 |
|  | $K_2CO_3$ | 27.60 |
| Eu', same precursor ratios as in Eu | $Li_2CO_3$ | 642.00 |
|  | $Na_2CO_3$ | 668.00 |
|  | $K_2CO_3$ | 690.00 |
| Cat. A' | $Cu_2(OH)_2CO_3$ | 25.00 |
|  | $Ce_2(CO_3)_3 \cdot xH_2O$ | 425.00 |
|  | Eu' | 1955.00 |
| Cat. A | $BaCO_3$ | 1.00 |
|  | $Cu_2(OH)_2CO_3$ | 1.00 |
|  | $Ce_2(CO_3)_3 \cdot xH_2O$ | 17.00 |
|  | Eu | 80.00 |
| Cat. B | $BaCO_3$ | 0.40 |
|  | $La(OH)_3$ | 0.40 |
|  | $FeCO_3$ | 6.80 |
|  | Eu | 80.00 |
| Cat. C | $BaCO_3$ | 0.40 |
|  | $MnCO_3$ | 7.20 |
|  | Eu | 80.00 |
| Cat. D | $(NH_4)_2MoO_4$ | 0.40 |
|  | $V_2O_5$ | 7.20 |
|  | Eu | 80.00 |
| Cat. E | $FeCO_3$ | 10.00 |
|  | $Cu_2(OH)_2CO_3$ | 10.00 |
|  | $(NH_4)_2MoO_4$ | 10.00 |
|  | Eu | 70.00 |
| Cat. F | $NiCO_3$ | 10.00 |
|  | $MnCO_3$ | 10.00 |
|  | $CoCO_3$ | 10.00 |
|  | Eu | 70.00 |

Example 2. Mini-Batch Reactor Screening Study

This example demonstrates that the use of invented catalyst in direct oxycracking of various carbon-containing feedstocks increases the extent of cracking and thereby, increases the yield to desired light olefins and aromatics.

Figure 5:
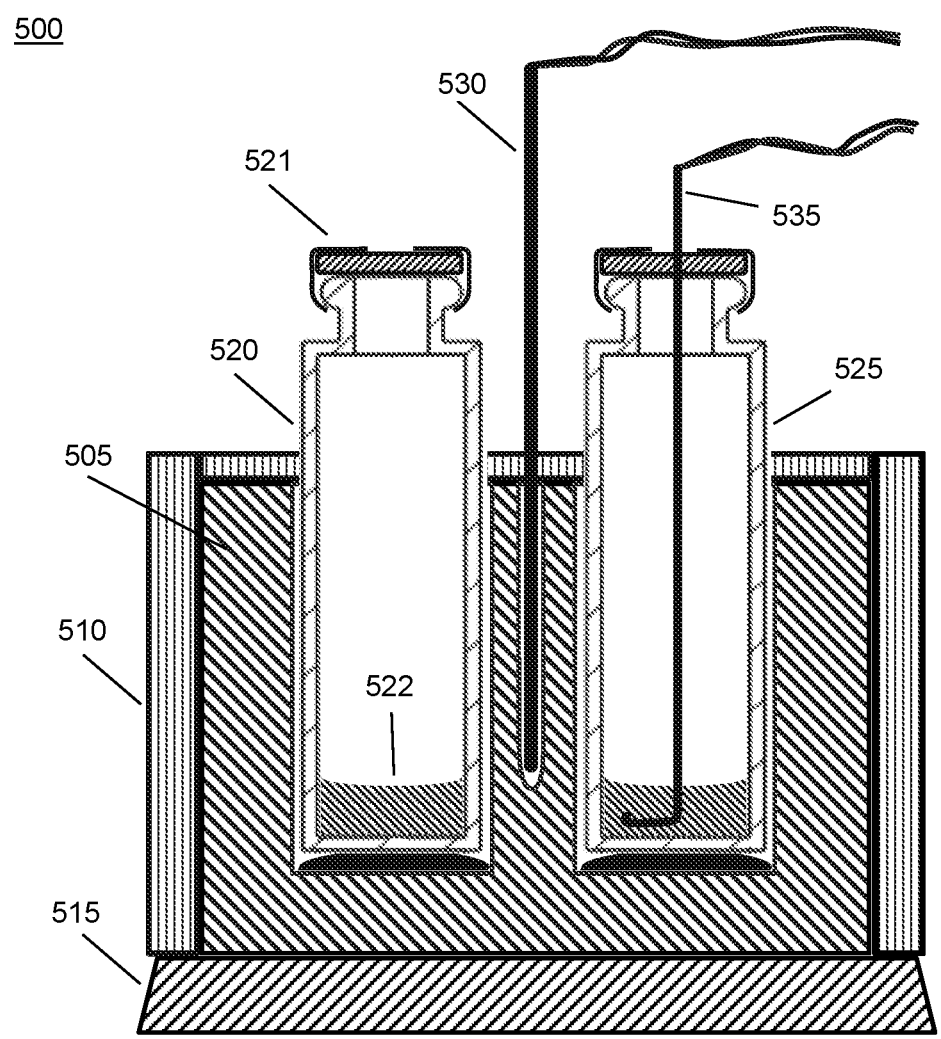
FIG. 5 is a schematic diagram of a batch reactor set-up, according to the examples.

Experimental setup description: Referring now to FIG. 5. The 23 mm diameter, 75 mm tall, and 20 ml volume round bottom clear borosilicate glass vials 520 (Ace Glass) make suitable mini-batch reactors for screening both catalysts and substrates in the oxycracking in molten salts. After loading with the desired amount of catalyst and reaction substrate 522, the vials were sealed with the 20 mm diameter crimp caps equipped with the PTFE-lined silicone septa 521 (Thermo Scientific™ SUN-SRi™). The reaction screening assembly consisted of a 6 parallel 25 mm diameter 50 mm deep channels aluminum alloy block 505 (Corning LSE Digital Dry Bath Accessory) insulated with the glass wool thermal insulation layer 510 and affixed on-top of a compact ceramic hot-plate 515 (Electron Microscopy Sciences with Corning Pyroceram heating element, model Pc220, 25-550° C. range). The set-up was located inside a vent hood behind a blast shield for enhanced operator safety. The temperature of the aluminum block 505 was controlled by powering the hot plate through an external temperature controller (not shown on the FIG. 5) (Chemglass Life Sciences J-Kem Temperature Controller, Model 210/T) equipped with a metal-jacketed ⅛" diameter K-type thermocouple 530 whose tip was inserted into the thermocouple channel in the aluminum block. The 3 grams of a 40 grit SiC powder were added to each of the 6 channels in the aluminum alloy block in order to provide better thermal contact between the vials and the block. A glass vial 525 was filled ~¼ of volume with the $Li_{0.86}Na_{0.64}K_{0.50}CO_3$ composition eutectic salts mixture and placed in one of the corner channels in the block. A K-type thermocouple 535 was inserted in the vial; with its tip immersed into the eutectic material at the bottom. The thermocouple was connected to a digital readout to indicate the temperature of reaction medium in the vials.

Experimental procedure description: A new glass vial is weighted; then loaded with 10-20 mg of a feedstock and 1100-1250 mg of molten salt catalyst powder; then, the reactor is sealed using a crimping tool in air for the direct oxycracking, or in the glove box under inert nitrogen atmosphere for the 2-step oxycracking. The vials are arranged in groups of 2, then loaded using a pair of forceps into the aluminum block that is maintained at 420° C. for the direct oxycracking, or 500° C. for the 2-step oxycracking. The vials are heated inside the alloy block for 15 min and then, removed and placed horizontally onto a glass wool blanket to cool. Once at near room temperature, the vials are placed into a vial holder array plate and stored in it until analysis. The analysis is performed using a GC instrument, and as a part of the analysis each vial is heated to 180° C. for 10 min before the vapor phase is sampled for analysis. The analysis is also performed using a separate GC-MS instrument for selected parallel reactor runs.

Product analysis description: Product composition was analyzed using an Agilent 8890 gas chromatograph equipped with a thermal conductivity detector (TCD) and flame ionization detector (FID). The identity of the compounds was determined either based on the mass-spectra signatures match with a NIST-MS database on a separate GC-MS instrument for all the compounds in the refinery gas standard (Restek Refinery Gas Standard #2, Manufacturer #34442) or based on the order of elution following the boiling point of the solutes/compounds (FID) and thermal conductivity differences (TCD). The peaks areas obtained by integrating peaks on the gas chromatogram were used in the quantification of hydrocarbon compounds (FID signal) and permanent gases (TCD signal). More specifically, the peak areas were converted to molar concentrations using the molar response factors (TCD and FID) of various alkane and alkene products estimated from GC calibration with the refinery gas standard sample, while molar or relative response factors (FID) of various aromatic products were estimated from theoretical effective carbon number approach (Journal of Chromatographic Science, Vol. 23, August, 1985). The following equation (10) was used to determine the yield (wt %) of a given compound.

$$\text{Yield(wt \%)} = \text{Weight(compound)}/\text{Weight(feed)} \times 100 \quad (10)$$

Figure 8:
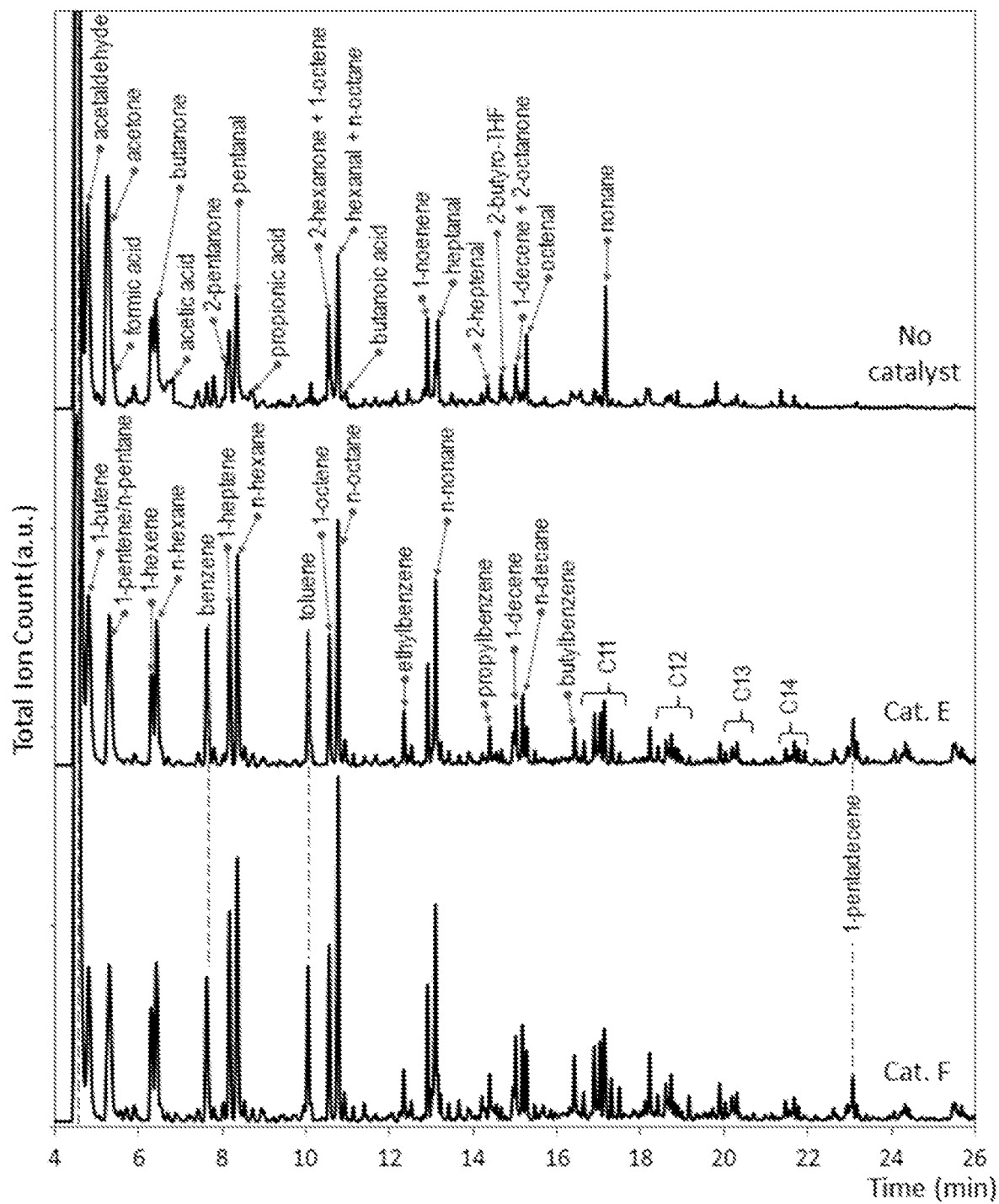
FIG. 8 includes GC-MS traces for the products collected direct oxycracking of olive oil without a catalyst, and with Cat. E and Cat. F in a mini-batch reactor, according to the examples.
Figure 9:
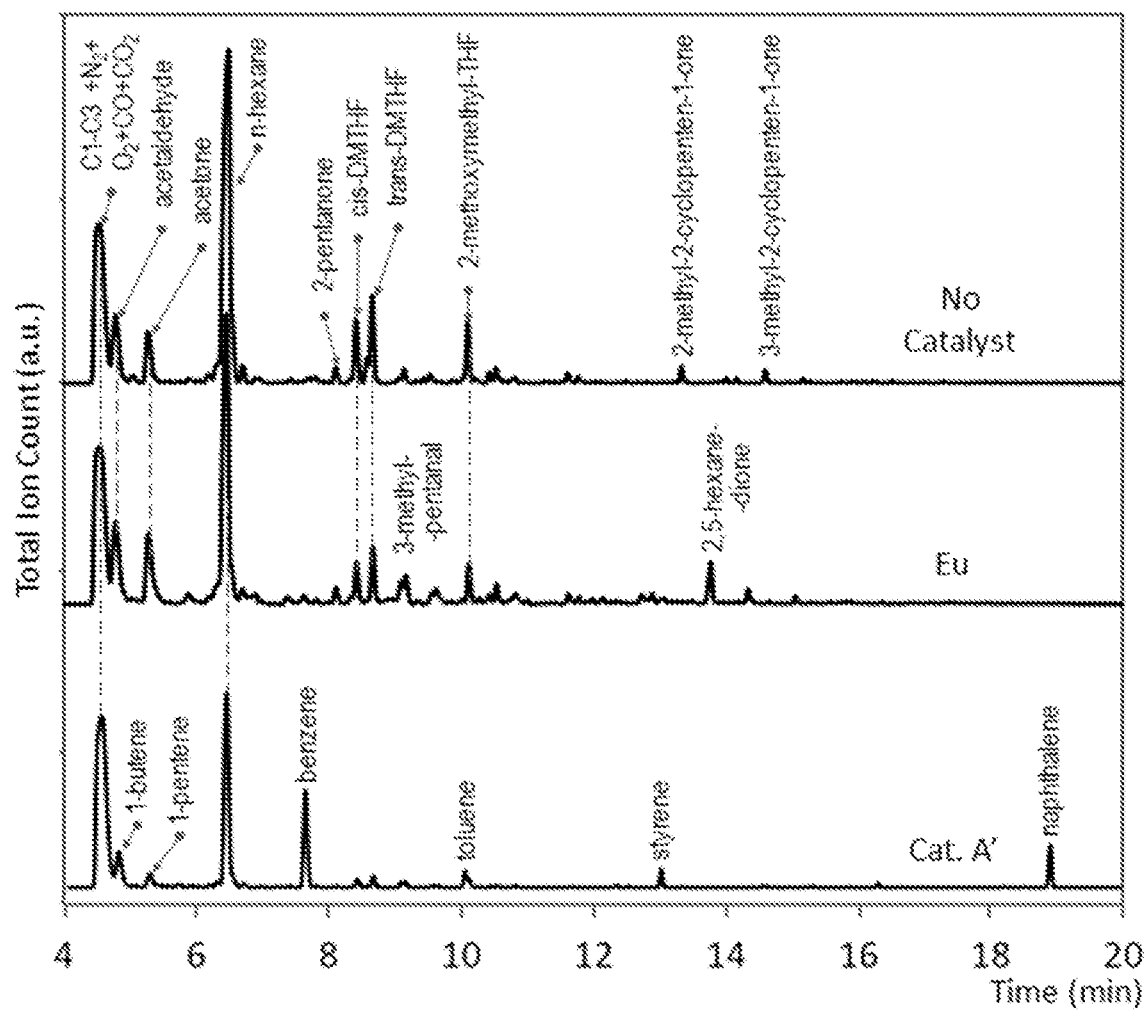
FIG. 9 includes GC-MS traces for the products collected from direct oxycracking of n-hexane in the presence of $Li_2CO_3$—$Na_2CO_3$—$K_2CO_3$ (43.5-31.5-25 mol %) eutectic mixture, and of Cat. A' in a mini-batch reactor, according to the examples.

The products obtained during direct oxycracking with Cat. A (from Table 3) were analyzed using GC, and the results are reported in Table 4, with product stream containing various alkanes, olefins, aromatics and oxygenates viz. hydrogen, methane, ethane, ethylene, propane, propylene, butanes, butenes, pentanes, pentenes, hexanes, carbon oxides and others. The use of catalyst resulted in higher conversions for all the feedstocks, increasing the overall yield to the desired light olefins and aromatics, though slightly decreasing the selectivity. Furthermore, the products obtained from parallel reactor runs were also analyzed using GC-MS to capture a much broader range of products. FIG. 8 and FIG. 9 includes the GC-MS traces for the products collected from direct oxycracking of olive oil with Cat. E and Cat. F and of n-hexane with Cat. A respectively.

TABLE 4

Product mixtures from thermal and catalytic direct oxycracking of HDPE and n-hexane feedstocks over Cat. A.

| Product Selectivity, | Feedstock: HDPE | | Feedstock: n-Hexane | |
|---|---|---|---|---|
| wt % of total gases | None | Cat. A | None | Cat. A |
| Hydrogen | — | — | — | 0.3 |
| Methane | 0.5 | 0.4 | 9.6 | 8.8 |
| Ethane | — | — | — | — |
| Ethylene | 1.5 | 0.9 | 7.6 | 13.3 |
| Propane | — | — | — | — |
| Propylene | 1.0 | 1.1 | 1.3 | 2.8 |
| Butanes | 0.3 | 0.4 | — | — |
| Butenes | 0.6 | 0.9 | 0.7 | 1.2 |
| Pentanes | — | — | — | — |
| Pentenes | 0.3 | 0.6 | 0.2 | 0.4 |
| Hexanes | 0.2 | 0.3 | 5.8 | 21.4 |
| Aromatics[a] | 0.6 | 2.0 | 3.0 | 2.5 |
| CO | 58.7 | 1.3 | 65.5 | 15.7 |
| $CO_2$ | 36.3 | 92.2 | 6.1 | 33.4 |
| Conversion[b] | 2.6 | 1.6 | 42.9 | 55.85 |

[a]Aromatics is a sum of content of benzene, ethylbenzene, toluene, styrene, xylenes.
[b]Conversion defined as the total amount of formed gaseous products to the amount of feed.

Example 3. Mini-Batch Reactor Screening Study

This example demonstrates that the use of invented catalyst in 2-step oxycracking of various carbon-containing feedstocks increases the extent of cracking and thereby, increases the yield to desired light olefins and aromatics.

Figure 11:
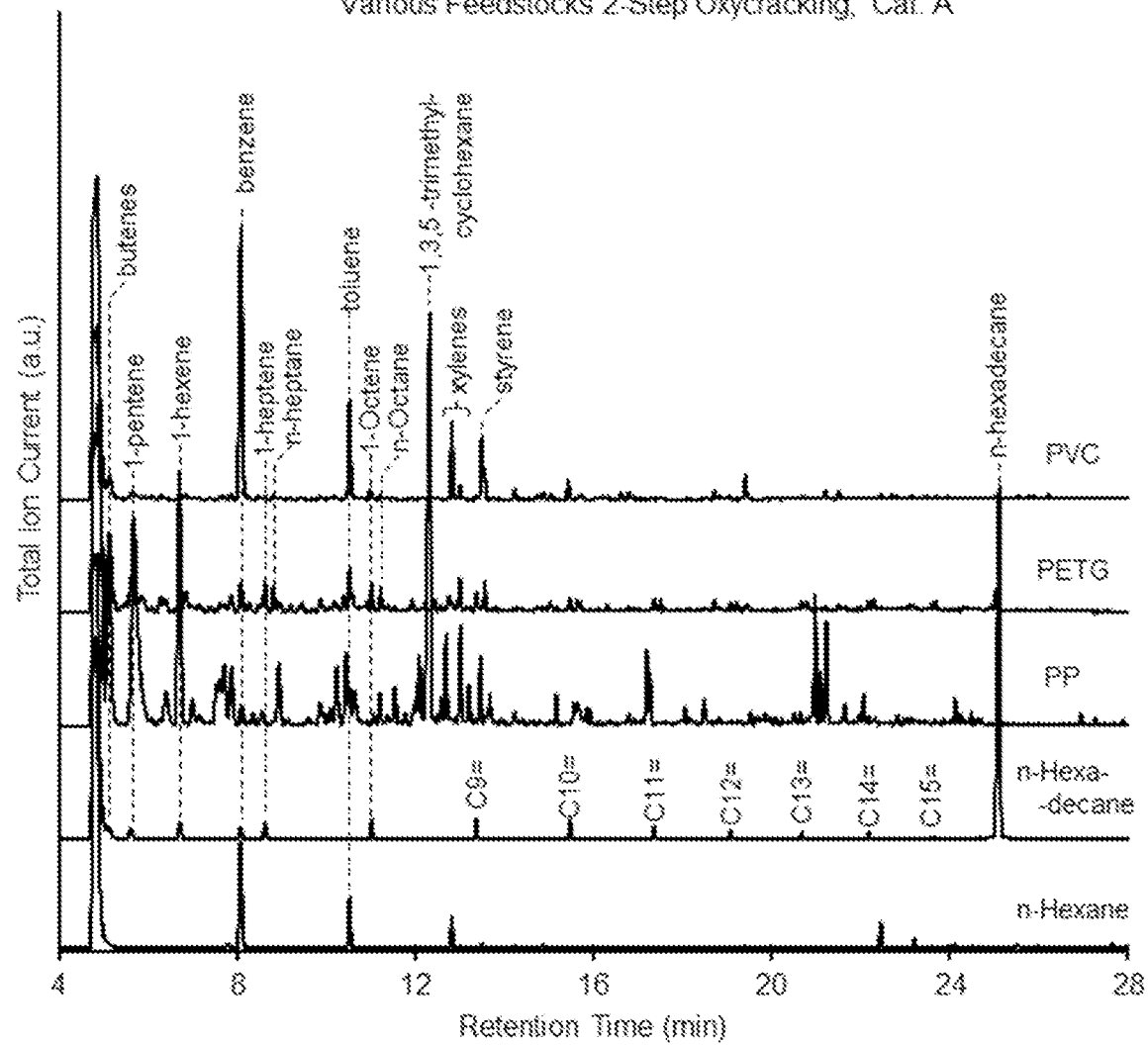
FIG. 11 includes GC-MS traces for the products collected from 2-step oxycracking of various feedstocks in the presence of Cat. A in a mini-batch reactor, according to the examples.

Using the same experimental setup described in example 2, the products obtained during 2-step oxycracking of wide range of feedstocks, including high-density polyethylene (HDPE), low-density polyethylene (LDPE), polypropylene (PP), polyethylene terephthalate glycol (PETG), polystyrene (PS), polyvinyl chloride (PVC), asphalt, vegetable oil (Veg Oil), n-hexane, n-hexadecane, paper, rubber, polyurethane (PU) and potato chips, with Cat. A (from Table 3) were analyzed using GC, and the results are reported in Tables 5A-5G. The use of catalyst resulted in higher conversions for all the feedstocks, increasing the overall yield to the desired light olefins and aromatics, though slightly decreasing the selectivity. Furthermore, the products obtained from parallel reactor runs were also analyzed using GC-MS to capture a much broader range of products. FIG. 11 includes the GC-MS traces for the products collected from 2-step oxycracking of n-hexane, n-hexadecane, PP, PETG and PVC with Cat. A. While the feedstocks like PETG and PVC contain heteroatoms like O and Cl, their oxycracking products do not comprise of O and Cl respectively (from FIG. 11). This highlights an additional significant advantage of the invented molten-based catalyst, wherein the molten phase eliminates or significantly decreases the emission of such heteroatom pollutants into the products or atmosphere by retaining the heteroatoms (like O, Cl, etc.) during the reaction step.

TABLE 5A

Product mixtures from thermal and catalytic 2-step oxycracking of HDPE and LDPE feedstocks over Cat. A.

| Product Selectivity, | Feedstock: HDPE | | Feedstock: LDPE | |
| --- | --- | --- | --- | --- |
| wt % of total gases | None | Cat. A | None | Cat. A |
| Hydrogen | — | 0.9 | — | 2.4 |
| Methane | 5.8 | 5.1 | 6.1 | 6.6 |
| Ethane | — | — | — | — |
| Ethylene | 19.5 | 13.4 | 16.9 | 16.5 |
| Propane | — | — | — | — |
| Propylene | 26.8 | 17.1 | 21.8 | 20.5 |
| Butanes | 5.6 | 2.2 | 7.3 | 4.0 |
| Butenes | 20.7 | 12.2 | 20.7 | 16.6 |
| Pentanes | — | — | — | 0.1 |
| Pentenes | 11.3 | 8.1 | 12.8 | 9.6 |
| Hexanes | 8.1 | 3.5 | 7.6 | 4.5 |
| Aromatics[a] | 2.1 | 6.5 | 6.9 | 10.6 |
| CO | — | 1.2 | — | 2.3 |
| $CO_2$ | — | 29.8 | — | 6.4 |
| Conversion[b] | 4.6 | 26.0 | 6.1 | 20.3 |

[a]Aromatics is a sum of content of benzene, ethylbenzene, toluene, styrene, xylenes.
[b]Conversion defined as the total amount of formed gaseous products to the amount of feed.

[b]Conversion defined as the total amount of formed gaseous products to the amount of feed.

Thus, 2-step oxycracking of HDPE and LDPE feedstocks over Cat. A resulted in increased cracking conversion to gaseous products from 4.6% to 26.0% and from 6.1% to 20.3% respectively, thereby increasing the overall yield to light olefins (more specifically, ethylene and propylene) and aromatics, albeit at the expense of slightly decreased selectivity.

TABLE 5B

Product mixtures from thermal and catalytic 2-step oxycracking of PP and PETG feedstocks over Cat. A.

| Product Selectivity, | Feedstock: PP | | Feedstock: PETG | |
| --- | --- | --- | --- | --- |
| wt % of total gases | None | Cat. A | None | Cat. A |
| Hydrogen | — | 0.3 | — | 0.5 |
| Methane | 4.3 | 2.0 | 38.9 | 1.0 |
| Ethane | — | — | 0.0 | — |
| Ethylene | 5.9 | 4.4 | 18.0 | 1.0 |
| Propane | — | — | — | — |
| Propylene | 38.8 | 27.3 | 3.9 | 0.3 |
| Butanes | 0.5 | 0.6 | — | — |
| Butenes | 22.8 | 16.8 | 1.7 | 0.1 |
| Pentanes | — | 0.1 | — | — |
| Pentenes | 17.6 | 31.3 | — | 0.2 |
| Hexanes | 4.4 | 3.2 | 0.2 | — |
| Aromatics[a] | 5.7 | 6.6 | 37.2 | 11.2 |
| CO | — | 0.5 | — | 7.1 |

TABLE 5B-continued

Product mixtures from thermal and catalytic 2-step oxycracking of PP and PETG feedstocks over Cat. A.

| Product Selectivity, | Feedstock: PP | | Feedstock: PETG | |
| --- | --- | --- | --- | --- |
| wt % of total gases | None | Cat. A | None | Cat. A |
| $CO_2$ | — | 6.9 | — | 78.5 |
| Conversion[b] | 17.4 | 44.6 | 3.4 | 40.9 |

[a]Aromatics is a sum of content of benzene, ethylbenzene, toluene, styrene, xylenes.
[b]Conversion defined as the total amount of formed gaseous products to the amount of feed.

Thus, 2-step oxycracking of PP and PETG feedstocks over Cat. A resulted in increased cracking conversion to gaseous products from 17.4% to 44.6% and from 3.4% to 40.9% respectively, thereby increasing the overall yield to light olefins (more specifically, ethylene and propylene) and aromatics, albeit at the expense of slightly decreased selectivity.

TABLE 5C

Product mixtures from thermal and catalytic 2-step oxycracking of PS and PVC feedstocks over Cat. A.

| Product Selectivity, | Feedstock: PS | | Feedstock: PVC | |
| --- | --- | --- | --- | --- |
| wt % of total gases | None | Cat. A | None | Cat. A |
| Hydrogen | — | — | 0.4 | 0.7 |
| Methane | — | 0.1 | 9.7 | 3.0 |
| Ethane | — | — | — | — |
| Ethylene | 1.1 | 0.2 | 4.8 | 1.7 |
| Propane | — | — | — | — |
| Propylene | 0.4 | 0.1 | 7.3 | 1.6 |
| Butanes | — | — | 1.3 | 0.5 |
| Butenes | 0.3 | 0.1 | 6.9 | 1.4 |
| Pentanes | 4.0 | 0.7 | — | — |
| Pentenes | — | — | 1.8 | 0.6 |
| Hexanes | — | — | 1.9 | 0.5 |
| Aromatics[a] | 94.3 | 53.7 | 65.9 | 25.7 |
| CO | — | 0.1 | — | 1.7 |
| $CO_2$ | — | 45.1 | — | 62.6 |
| Conversion[b] | 6.9 | 38.1 | 8.7 | 23.4 |

[a]Aromatics is a sum of content of benzene, ethylbenzene, toluene, styrene, xylenes.
[b]Conversion defined as the total amount of formed gaseous products to the amount of feed.

Thus, 2-step oxycracking of PS and PVC feedstocks over Cat. A resulted in increased cracking conversion to gaseous products from 6.9% to 38.1% and from 8.7% to 23.4% respectively, thereby increasing the overall yield to light olefins (more specifically, ethylene and propylene) and aromatics, albeit at the expense of slightly decreased selectivity.

TABLE 5D

Product mixtures from thermal and catalytic 2-step oxycracking of asphalt and vegetable oil feedstocks over Cat. A.

| Product Selectivity, | Feedstock: Asphalt | | Feedstock: Veg Oil | |
| --- | --- | --- | --- | --- |
| wt % of total gases | None | Cat. A | None | Cat. A |
| Hydrogen | — | 2.3 | 0.2 | 4.4 |
| Methane | 21.4 | 16.7 | 5.0 | 6.0 |
| Ethane | — | — | — | — |
| Ethylene | 9.6 | 12.6 | 8.2 | 8.3 |
| Propane | — | — | — | — |
| Propylene | 15.0 | 18.5 | 10.8 | 13.0 |
| Butanes | 5.0 | 3.9 | 2.1 | 3.6 |
| Butenes | 13.6 | 14.1 | 8.3 | 9.9 |
| Pentanes | 1.1 | 0.9 | — | 0.1 |
| Pentenes | 6.2 | 7.4 | 25.2 | 33.7 |

TABLE 5D-continued

Product mixtures from thermal and catalytic 2-step oxycracking of asphalt and vegetable oil feedstocks over Cat. A.

| Product Selectivity, | Feedstock: Asphalt | | Feedstock: Veg Oil | |
|---|---|---|---|---|
| wt % of total gases | None | Cat. A | None | Cat. A |
| Hexanes | 8.7 | 6.5 | 4.3 | 5.6 |
| Aromatics[a] | 13.8 | 13.8 | 6.1 | 9.7 |
| CO | — | 3.3 | — | 5.8 |
| $CO_2$ | 5.4 | — | 29.8 | — |
| Conversion[b] | 5.9 | 11.8 | 28.9 | 32.4 |

[a]Aromatics is a sum of content of benzene, ethylbenzene, toluene, styrene, xylenes.
[b]Conversion defined as the total amount of formed gaseous products to the amount of feed.

Thus, 2-step oxycracking of Asphalt and Veg Oil feedstocks over Cat. A resulted in increased cracking conversion (and selectivity) to gaseous products from 5.9% to 11.8% and from 28.9% to 32.4% respectively, thereby increasing the overall yield to light olefins (more specifically, ethylene and propylene) and aromatics.

TABLE 5E

Product mixtures from thermal and catalytic 2-step oxycracking of n-hexane and n-hexadecane feedstocks over Cat. A.

| Product Selectivity, | Feedstock: n-hexane | | Feedstock: n-hexadecane | |
|---|---|---|---|---|
| wt % of total gases | None | Cat. A | None | Cat. A |
| Hydrogen | — | — | — | — |
| Methane | 0.2 | 0.4 | 8.5 | 3.2 |
| Ethane | — | — | — | — |
| Ethylene | 0.4 | 0.6 | 27.8 | 10.2 |
| Propane | — | — | — | — |
| Propylene | 0.5 | 1.0 | 22.1 | 8.0 |
| Butanes | — | — | — | — |
| Butenes | 0.5 | 0.7 | 15.5 | 5.5 |
| Pentanes | — | — | — | — |
| Pentenes | — | — | 14.8 | 5.1 |
| Hexanes | 98.5 | 97.4 | 0.2 | 0.1 |
| Aromatics[a] | — | — | 11.0 | 4.3 |
| CO | — | — | — | — |
| $CO_2$ | — | — | 0.1 | 63.6 |
| Conversion[b] | 1.6 | 2.7 | 6.4 | 16.8 |

[a]Aromatics is a sum of content of benzene, ethylbenzene, toluene, styrene, xylenes.
[b]Conversion defined as the total amount of formed gaseous products to the amount of feed.

Thus, 2-step oxycracking of n-hexane and n-hexadecane feedstocks over Cat. A resulted in increased cracking conversion to gaseous products from 1.6% to 2.7% and from 6.4% to 16.8% respectively, thereby increasing the overall yield to light olefins (more specifically, ethylene and propylene) and aromatics, albeit at the expense of slightly decreased selectivity for the case of n-hexadecane feedstock.

TABLE 5F

Product mixtures from thermal and catalytic 2-step oxycracking of paper and rubber feedstocks over Cat. A.

| Product Selectivity, | Feedstock: Paper | | Feedstock: Rubber | |
|---|---|---|---|---|
| wt % of total gases | None | Cat. A | None | Cat. A |
| Hydrogen | — | 0.6 | — | 1.3 |
| Methane | 31.5 | 1.5 | 10.8 | 10.0 |
| Ethane | 0.0 | — | — | — |
| Ethylene | 7.8 | 0.4 | 5.3 | 6.2 |
| Propane | — | — | — | — |
| Propylene | 12.5 | 0.4 | 7.6 | 9.2 |
| Butanes | 1.8 | 0.1 | 1.4 | 1.5 |
| Butenes | 12.6 | 0.2 | 7.4 | 7.3 |
| Pentanes | 0.2 | — | 0.2 | 0.2 |
| Pentenes | 3.7 | — | 5.9 | 4.7 |
| Hexanes | 8.0 | 0.1 | 19.2 | 16.8 |
| Aromatics[a] | 22.0 | 0.6 | 42.2 | 40.0 |
| CO | — | 1.2 | — | 2.7 |
| $CO_2$ | — | 95.0 | — | — |
| Conversion[b] | 3.1 | 31.7 | 16.1 | 16.5 |

[a]Aromatics is a sum of content of benzene, ethylbenzene, toluene, styrene, xylenes.
[b]Conversion defined as the total amount of formed gaseous products to the amount of feed.

Thus, 2-step oxycracking of paper and rubber feedstocks over Cat. A resulted in increased cracking conversion to gaseous products from 3.1% to 31.7% and from 16.1% to 16.5% respectively, thereby increasing the overall yield to light olefins (more specifically, ethylene and propylene) and aromatics, albeit at the expense of slightly decreased selectivity for the case of paper feedstock.

TABLE 5G

Product mixtures from thermal and catalytic 2-step oxycracking of PU and potato chips feedstocks over Cat. A.

| Product Selectivity, | Feedstock: PU | | Feedstock: Chips | |
|---|---|---|---|---|
| wt % of total gases | None | Cat. A | None | Cat. A |
| Hydrogen | — | 7.2 | — | 2.1 |
| Methane | 7.8 | 2.2 | 23.8 | 5.4 |
| Ethane | — | — | — | — |
| Ethylene | 6.6 | 2.6 | 12.1 | 4.3 |
| Propane | — | — | — | — |
| Propylene | 47.6 | 5.9 | 15.0 | 5.4 |
| Butanes | 1.6 | 0.1 | 3.8 | 1.8 |
| Butenes | 25.4 | 4.3 | 13.4 | 4.3 |
| Pentanes | — | — | 0.2 | 0.1 |
| Pentenes | 0.9 | 0.4 | 6.3 | 2.8 |
| Hexanes | 3.0 | 0.9 | 8.7 | 2.2 |
| Aromatics[a] | 7.0 | 3.6 | 16.7 | 7.4 |
| CO | — | 15.8 | — | 6.6 |
| $CO_2$ | — | 56.9 | — | 57.7 |
| Conversion[b] | 6.5 | 15.5 | 6.0 | 19.5 |

[a]Aromatics is a sum of content of benzene, ethylbenzene, toluene, styrene, xylenes.
[b]Conversion defined as the total amount of formed gaseous products to the amount of feed.

Thus, 2-step oxycracking of PU and potato chips feedstocks over Cat. A resulted in increased cracking conversion to gaseous products from 6.5% to 15.5% and from 6.0% to 19.5% respectively, thereby increasing the overall yield to light olefins (more specifically, ethylene and propylene) and aromatics, albeit at the expense of slightly decreased selectivity.

Example 4. Mini-Batch Reactor Screening Study

This example demonstrates the use of various types of invented catalysts in 2-step oxycracking to tune the product stream/distribution towards light olefins and aromatics.

Figure 10:
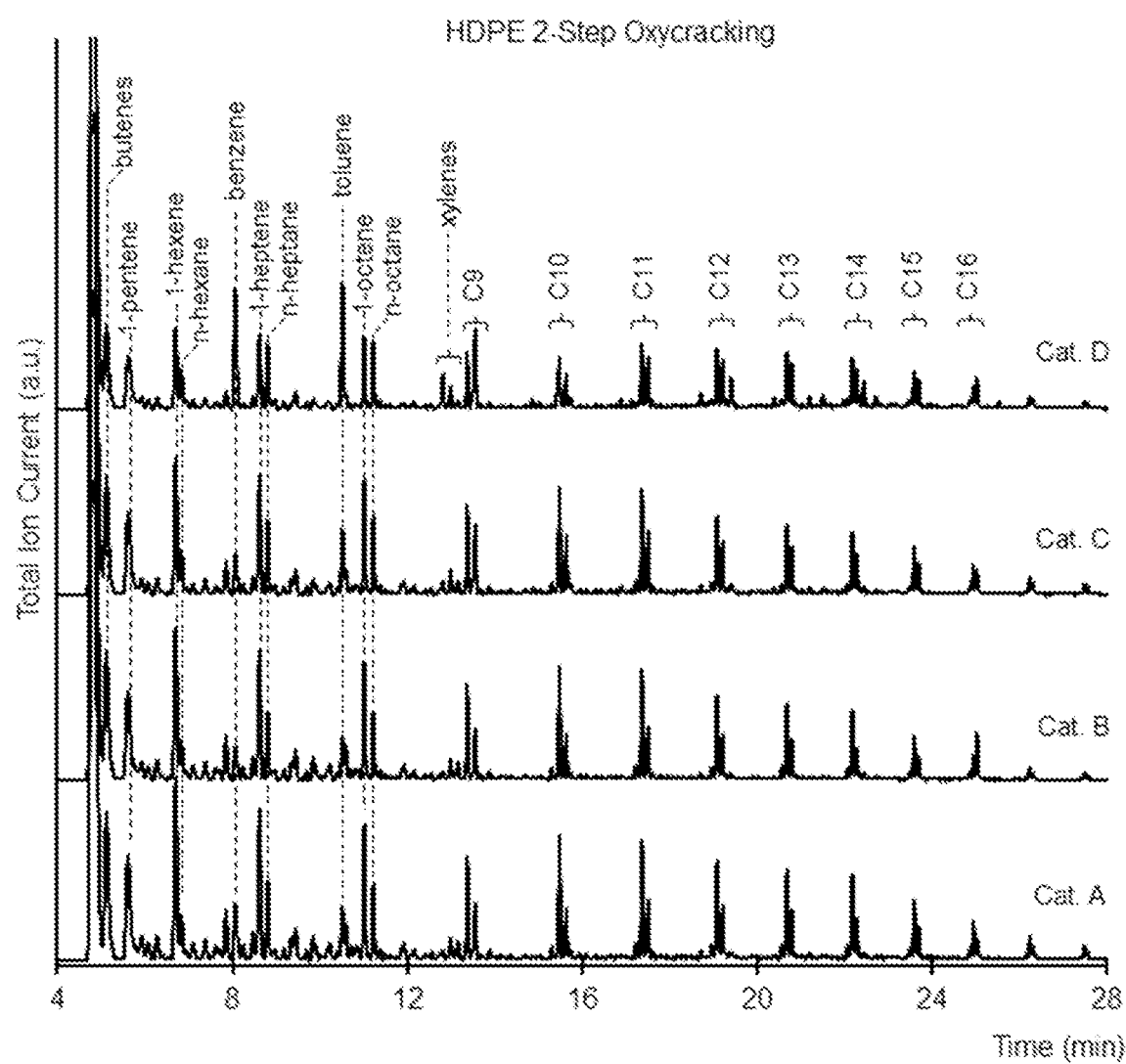
FIG. 10 includes GC-MS traces for the products collected from 2-step oxycracking of HDPE in the presence of Cat. A, Cat. B, Cat. C, and Cat. D, in a mini-batch reactor according to the examples.

Using the same experimental setup described in example 2, the products obtained during 2-step oxycracking of HDPE feedstock with Cat. A, Cat. B and Cat. C (from Table 3) were analyzed using GC, and the results are reported in Table 6. The product distribution (more specifically, light olefins and aromatics) is found to be a strong function of the type of catalyst. Furthermore, the products obtained from parallel reactor runs were also analyzed using GC-MS to capture a much broader range of products. FIG. 10 includes the GC-MS traces for the products collected from 2-step oxycracking of HDPE with Cat. A, Cat. B, Cat. C and Cat. D.

TABLE 6

Product mixtures from thermal and catalytic 2-step oxycracking of HDPE feedstock over various catalysts (Cat. A, Cat. B, Cat. C).

| Product Selectivity, | Feedstock: HDPE | | | |
|---|---|---|---|---|
| wt % of total gases | None | Cat. A | Cat. B | Cat. C |
| Hydrogen | — | 0.9 | — | — |
| Methane | 5.8 | 5.1 | 4.7 | 1.2 |
| Ethane | — | — | — | — |
| Ethylene | 19.5 | 13.4 | 12.3 | 3.2 |
| Propane | — | — | — | — |
| Propylene | 26.8 | 17.1 | 15.9 | 4.0 |
| Butanes | 5.6 | 2.2 | 2.0 | 0.6 |
| Butenes | 20.7 | 12.2 | 11.3 | 3.0 |
| Pentanes | — | — | — | — |
| Pentenes | 11.3 | 8.1 | 7.2 | 1.9 |
| Hexanes | 8.1 | 3.5 | 3.5 | 0.9 |
| Aromatics[a] | 2.1 | 6.5 | 6.5 | 1.4 |
| CO | — | 1.2 | 0.8 | 0.1 |
| $CO_2$ | — | 29.8 | 35.8 | 83.8 |
| Conversion[b] | 4.6 | 26.0 | 29.1 | 85.8 |

[a]Aromatics is a sum of content of benzene, ethylbenzene, toluene, styrene, xylenes.
[b]Conversion defined as the total amount of formed gaseous products to the amount of feed.

While the cracking conversion to gaseous products from 2-step oxycracking of HDPE feedstock increased from Cat. A to Cat. B to Cat. C, the selectivity to desired light olefins (more specifically, ethylene and propylene) decreased from Cat A. to Cat. B to Cat. C, and thus, resulting in different overall yields to light olefins and aromatic for Cat. A, Cat. B and Cat. C.

Example 5. Bench-Scale Stirred Tank Reactor Study

Liquid n-hexadecane feedstock was introduced via a syringe pump (Teledyne ISCO 1000D) at a rate of 0.77 gram per minute together with 400 standard centimeter cube per minute (sccm) flow of $N_2$ diluent through a 0.95 centimeter diameter stainless steel dip tube. The dip tube terminated near the bottom of a 10.0 centimeter diameter and 62.2 centimeter height stainless steel stirred tank reactor. The reactor contained 2316 gram a molten catalyst, Cat. A', under a constant stirring by a 5 centimeter diameter three-blade hydrofoil impeller located at the bottom of the molten catalyst bath and operated at 200 rotations per minute. The height of the molten catalyst bath was about 14 centimeters, while the overall height of reactor heated to the reaction temperature was about 28 centimeters. The molten salt catalyst was prepared inside the reactor prior to the experiment by first loading the reactor with 1930 gram of the alkali-carbonate salts eutectic precursors mixture powder, then melting the powder into a molten eutectic by heating it to 450° C., then by adding 386 gram of the metal catalyst precursor powder into the molten salt eutectic under stirring and $N_2$ diluent purging. The catalyst was conditioned prior to oxycracking reactor experiment by heating the reactor to 750° C. under 2000 sccm flow of air, and maintaining it at the temperature for 2 hours. Then, the gas feed was switched to 400 sccm flow of $N_2$ diluent, and the reactor was allowed to cool to a desired reaction temperature. The molten salt catalyst temperature was monitored by a K-type thermocouple inserted through an access port at the bottom of the reactor, located just beneath the stirring impeller. The effluent gas flow first passed through a stainless steel condenser that was maintained at 5-15° C., then through a zone of sampling ports of the on-line process GC (Agilent 8890), and in-line process mass-spectrometer (MS, Pfeiffer Vacuum ThermoStar), before passing through a mineral oil bubbler, then vented into the atmosphere. The process GC was an identical instrument to the one used in the mini-batch reactor screening study. It was calibrated using a similar gas standard (Restek Refinery Gas Standard #2), which was also used for calibrating the process MS instrument. The content of the residual coke in the catalyst was obtained by integrating the 14 amu/z and 44 amu/z signals corresponding to $N_2$ and $CO_2$ ionized species concentration in the signal obtained from the process MS output. The quantity of liquid products accumulating in the condenser was measured gravimetrically. The duration of the oxycracking reaction step was 20 min, after which the feed of the liquid was discontinued and the reactor was purged with $N_2$ dilutant at 400 sccm for 15 minutes. Then, the $N_2$ flow rate was then increased to 2000 sccm for an additional 10 minutes to remove any residual volatile materials from the internal volume of the reactor. After the purge was completed, the catalyst regeneration step was performed by feeding air into the reactor through the dip tube at 900 sccm for 20-30 min duration, re-oxidizing the molten catalyst and combusting the residual coke. The furnace temperature was maintained the same between the oxycracking and catalyst regeneration reaction steps.

TABLE 7

Product composition from catalytic 2-step oxycracking of n-hexadecane in the presence of molten salt catalyst, Cat. A', in a stirred tank reactor at four different reaction temperatures.

| Product Yield, wt % | Temperature, C. | | | |
|---|---|---|---|---|
| on Feed | 500 | 600 | 650 | 700 |
| Hydrogen | — | 0.1 | 0.2 | 0.4 |
| Methane | 0.3 | 6.2 | 11.8 | 17.9 |
| Ethane | 0.7 | 7.2 | 10.9 | 11.9 |
| Ethylene | 0.8 | 17.7 | 25.9 | 28.9 |
| Propane | 0.4 | 1.1 | 1.7 | 1.4 |
| Propylene | 0.9 | 15.4 | 22.8 | 19.7 |
| Butanes | 0.1 | 0.2 | 0.3 | 0.2 |
| Butenes | 0.6 | 9.5 | 10.8 | 7.0 |
| Pentanes | — | 0.1 | 0.2 | 0.1 |
| Pentenes | 0.7 | 5.8 | 4.4 | 1.6 |
| Hexanes | — | 0.0 | 1.8 | 1.9 |
| Hexenes | 0.9 | 4.9 | 3.1 | 0.7 |
| Aromatics[a] | — | 1.1 | 5.1 | 9.8 |
| CO | — | — | — | 0.2 |
| $CO_2$ | — | 0.6 | 0.9 | 1.6 |
| Coke | — | 0.8 | 1.8 | 2.4 |
| Liquids | 94.6 | 34.7 | 4.0 | 0.6 |

[a]Aromatics is a sum of content of benzene, ethylbenzene, toluene, styrene, xylenes.

A summary of results of the 2-step oxycracking of n-hexadecane using a molten salt catalyst which contains a copper-cerium metal catalyst composition, is presented in Table 7. The results indicate a high yield of light olefins and high conversion of the feedstock that can be obtained when using the molten salt composition and process when performing the process at temperatures at above 600° C. and at below 700° C.

Example 6. Bench-Scale Stirred Tank Reactor Study

Solid polymer feedstocks were introduced via a generic 3D printer head feeder as a 1.75 millimeter diameter filament at a rate in the range between 0.75 and 1.4 gram per minute together with 400 sccm flow of $N_2$ diluent which were either co-fed through the dip tube, or were fed separately: the diluent through the dip tube and the polymer filament was fed from the headspace above the molten catalyst bath. The plastic feedstocks used in the experiment included: including high-density polyethylene (HDPE), polypropylene (PP), polyethylene terephthalate glycol (PETG), and acrylonitrile butadiene styrene (ABS).

TABLE 8

Product composition from catalytic 2-step oxycracking of various carbon-containing feedstocks: HDPE. PP, PETG, and ABS over the Cat. A' formulation at 650° C.

| Product Yield, wt% on Feed | Feedstock | | | |
| --- | --- | --- | --- | --- |
| | HDPE | PP | PETG | ABS |
| Hydrogen | 0.2 | 0.3 | 0.2 | 0.6 |
| Methane | 6.8 | 13.1 | 2.0 | 5.1 |
| Ethane | 4.5 | 7.7 | 0.3 | 2.3 |
| Ethylene | 13.7 | 12.1 | 1.4 | 5.7 |
| Propane | 1.0 | 2.7 | — | 0.5 |
| Propylene | 12.9 | 21.6 | 0.4 | 4.4 |
| Butanes | 0.2 | 0.7 | 0.8 | 0.1 |
| Butenes | 5.9 | 14.6 | 0.3 | 3.2 |
| Pentanes | 0.2 | 1.0 | 0.1 | 0.1 |
| Pentenes | 1.2 | 4.3 | 0.2 | 0.5 |
| Hexanes | 0.1 | 0.1 | 0.0 | — |
| Hexenes | 0.8 | 0.3 | 0.0 | 0.3 |
| Aromatics[a] | 9.0 | 6.4 | 21.4 | 6.8 |
| CO | 0.0 | 0.0 | 18.6 | 1.6 |
| $CO_2$ | 1.2 | 4.7 | 89.1 | 7.4 |
| Coke | 2.4 | 2.8 | 3.1 | 4.4 |
| Liquids | 40.7 | 16.0 | 42.5 | 68.3 |
| Feed rate, g/min | 1.38 | 0.83 | 0.93 | 0.79 |

[a]Aromatics is a sum of content of benzene, ethylbenzene, toluene, styrene, xylenes.

Figure 12:
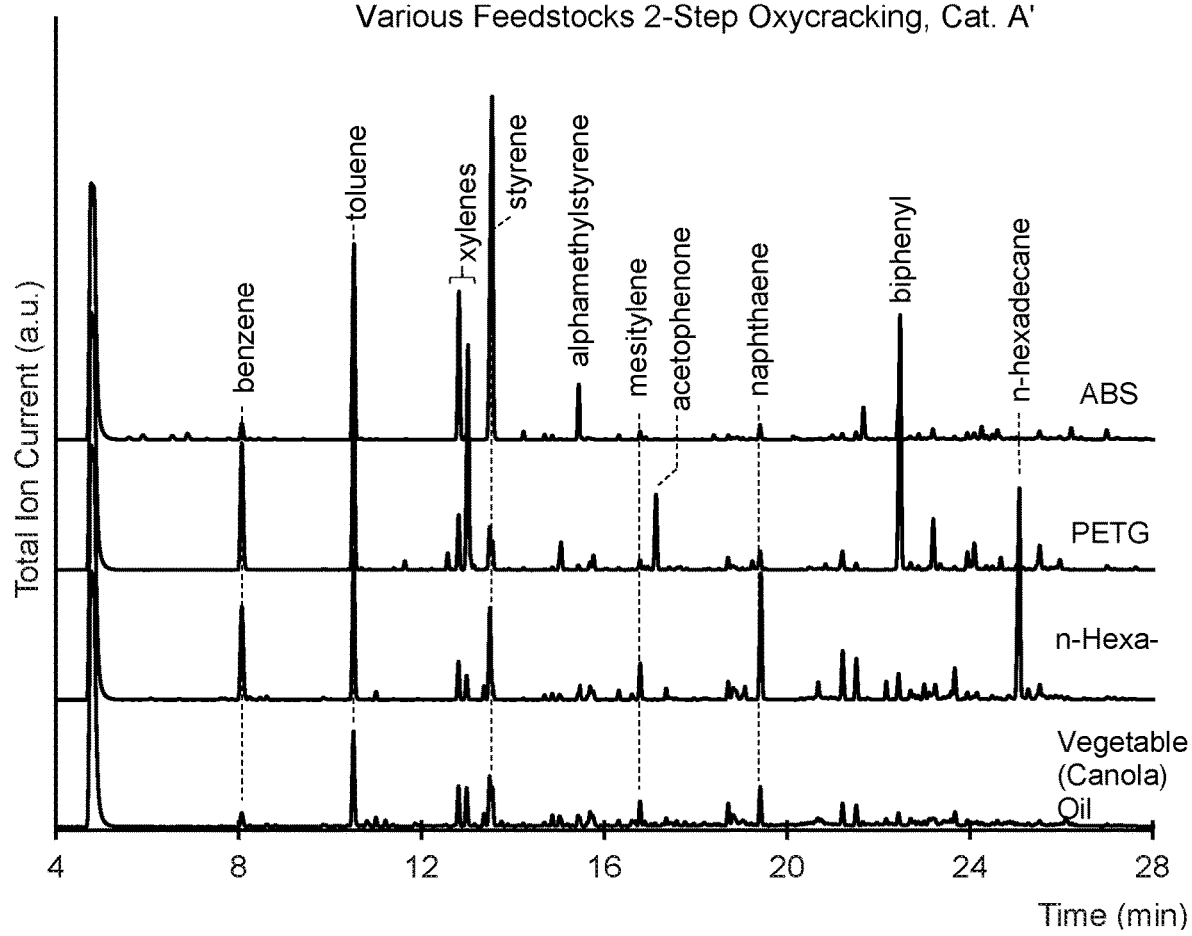
FIG. 12 includes GC-MS traces of liquid products collected from a 2-step oxycracking process that was performed in a stirred tank reactor in the presence of Cat. A', according to examples.

The products obtained during 2-step oxycracking were analyzed using GC, and the results are reported in Table 8. The liquid products composition for selected experiments was analyzed using the headspace GC-MS analysis (FIG. 12). The use of the oxycracking process with the molten salt catalyst affords high extents of conversion to vapor-phase products, which are dominated by light olefins and aromatic compounds. For instance, the 2-step oxycracking of polyolefinic feedstocks: HDPE and PP, produced high yields of light olefins. The processing of styrene-containing co-polymer produced primarily light aromatics, including the styrene monomer, while the processing of PETG also produced mostly aromatics, plus only a minor amounts of actophenone, and no appreciable amounts of other oxygenated organic products.

While certain embodiments have been illustrated and described, it should be understood that changes and modifications may be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations may be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like, include the number recited and refer to ranges which may be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process for the catalytic cracking of a carbon-containing feedstock, the process comprising:
    contacting, in a reactor system, the carbon-containing feedstock with a heterogeneous catalyst composition, said contacting occurring in the presence of an oxidant, to generate a product chemical compound; and
    collecting the product chemical compound, wherein:
the heterogeneous catalyst composition comprises a metal catalyst dispersed in a molten salt matrix comprising a eutectic mixture of alkali metal or alkaline earth metal carbonates or hydroxides; and
the metal catalyst comprises a transition metal compound and a rare-earth metal compound.

2. The process of claim 1, which is an autothermal process.

3. The process of claim 1, wherein the contacting is conducted at a temperature of about 750° C. or less.

4. The process of claim 1, which is a continuous process, a semi-continuous process, or a batch process.

5. The process of claim 1, wherein the product chemical compound comprises light olefins, α-olefins, terminal dienes, substituted and unsubstituted aromatic compounds, aldehydes, oxygenates, or a combination thereof.

6. The process of claim 1, wherein the product chemical compound comprises ethene, propene, 1-butene, 2-methyl-but-1-ene, 1-n-pentene, 1-n-hexene, 2-methyl-pent-1-ene, 3-methyl-pent-1-ene, 1,3-butadiene, 1,3-pentadiene, 1,4-pentadiene, 1,3-hexadiene, 1,4-hexadiene, 1,5-hexadiene, benzene, toluene, ethylbenzene, xylenes, styrene, α-methylstyrene, naphthalene, anthracene, or a combination thereof.

7. The process of claim 1, wherein the carbon-containing feedstock comprises a polymer comprising polyethylene, polypropylene, polyisobutylene, polybutadiene, polystyrene, poly-α-methylstyrene, polacrylates, poly(meth)acrylates, polyvinylchloride, polyethylene terephthalate, or a mixture of any two or more thereof.

8. The process of claim 1, wherein the carbon-containing feedstock comprises a refinery range hydrocarbon comprising asphalt, vacuum resid, heavy residual oil, paraffin wax, pyrolysis wax, lubricating oil, diesel, kerosene, naphtha, gasoline, or a combination thereof.

9. The process of claim 1, wherein the carbon-containing feedstock comprises a refinery range hydrocarbon comprising n-hexane.

10. The process of claim 1, wherein the carbon-containing feedstock comprises a refinery range hydrocarbon comprising n-hexadecane.

11. The process of claim 1, wherein the carbon-containing feedstock comprises lignin, fatty acid, plant-based oil, municipal solid waste, paper waste, or a mixture of any two or more thereof.

12. The process of claim 1, wherein the oxidant comprises at least one member selected from the group consisting of $O_2$, $NO_x$, $SO_x$, a nitrate salt, hydrogen peroxide, an organic peroxide, and a non-metal element oxide, such as boron oxide, nitrogen oxide, phosphorus oxide, sulfur oxide, chlorine oxide, and bromine oxide.

13. The process of claim 1, wherein the oxidant is oxygen and is introduced to the reactor as a purified $O_2$ stream, air, or a mixture of $O_2$ or air with a diluent, wherein the diluent is methane, carbon dioxide, nitrogen, argon, helium, or a mixture thereof.

14. The process of claim 1, wherein the reactor system comprises a single reactor or at least a first reactor and a second reactor in series.

15. The process of claim 1, wherein the reactor system comprises a single reactor, and the heterogeneous catalyst is contacted with the carbon-containing feedstock.

16. The process of claim 1, wherein the reactor system comprises a first reactor and a second reactor in series, and a heterogeneous catalyst composition in the first reactor is the same as or different than a heterogeneous catalyst composition in the second reactor.

17. The process of claim 1, wherein the heterogeneous catalyst composition is prepared outside of the reactor system; then loaded into the reactor system to carry out the catalytic cracking of hydrocarbons.

18. The process of claim 1, wherein the heterogeneous catalyst is prepared inside the reactor system, by loading the reactor system volume with a catalyst precursor mixture and heating it internally at the process temperature, and wherein the catalyst precursor mixture comprises a salt matrix comprising a eutectic mixture of alkali metal or alkaline earth metal carbonates or hydroxides and a metal catalyst precursor comprising a transition metal compound and a rare-earth metal compound.

19. The process of claim 18, wherein the metal catalyst precursor comprises a carbonate of Ce.

20. The process of claim 18, wherein the metal catalyst precursor comprises Cu and Ce carbonates, and the salt matrix comprises a mixture of Li, Na, and K carbonates or hydroxides.

21. The process of claim 18, wherein the metal catalyst precursor comprises a mixture of $Cu_2(OH)_2CO_3$ and $Ce_2(CO_3)_3 \cdot xH_2O$, and the salt matrix comprises of a mixture of $Li_2CO_3$, $Na_2CO_3$, and $K_2CO_3$.

22. The process of claim 18, wherein the metal catalyst precursor comprises a mixture of $CuCO_3$ and $Ce(CO_3)_2$, and the salt matrix comprises of a mixture of $Li_2CO_3$, $Na_2CO_3$, and $K_2CO_3$.

23. The process of claim 1, wherein the metal catalyst comprises Cu and Ce in a mol % ratio of about 0.10-0.20: 1.00, respectively.

* * * * *